United States Patent
Palikaras et al.

(10) Patent No.: US 11,298,052 B2
(45) Date of Patent: Apr. 12, 2022

(54) SENSOR

(71) Applicant: Medical Wireless Sensing Ltd, London (GB)

(72) Inventors: Georgios Palikaras, London Greater London (GB); Efthymios Kallos, London Greater London (GB); Helena Cano Garcia, London Greater London (GB)

(73) Assignee: MEDICAL WIRELESS SENSING LTD., London (GB)

( * ) Notice: Subject to any disclaimer, the term of this patent is extended or adjusted under 35 U.S.C. 154(b) by 427 days.

(21) Appl. No.: 15/121,364

(22) PCT Filed: Feb. 26, 2015

(86) PCT No.: PCT/GB2015/050561
§ 371 (c)(1),
(2) Date: Aug. 24, 2016

(87) PCT Pub. No.: WO2015/128657
PCT Pub. Date: Sep. 3, 2015

(65) Prior Publication Data
US 2016/0361002 A1    Dec. 15, 2016

(30) Foreign Application Priority Data

Feb. 26, 2014 (GB) ................................. 1403389

(51) Int. Cl.
*A61B 5/0507* (2021.01)
*A61B 5/053* (2021.01)
(Continued)

(52) U.S. Cl.
CPC .......... *A61B 5/14532* (2013.01); *A61B 5/053* (2013.01); *A61B 5/0507* (2013.01);
(Continued)

(58) Field of Classification Search
None
See application file for complete search history.

(56) References Cited

U.S. PATENT DOCUMENTS

| | | |
|---|---|---|
| 5,704,355 A | 1/1998 | Bridges |
| 6,768,051 B2 | 7/2004 | Wiltshire |

(Continued)

FOREIGN PATENT DOCUMENTS

| | | |
|---|---|---|
| CN | 1 700 034 A | 11/2005 |
| DE | 2736380 A1 | 2/1979 |

(Continued)

OTHER PUBLICATIONS

International Search Report for Inter'l Application No. PCT/GB2015/050561, filed Feb. 26, 2015, entitled "Sensor", dated Mar. 6, 2015.

(Continued)

*Primary Examiner* — Jay B Shah
(74) *Attorney, Agent, or Firm* — Polsinelli LLP; Kory D. Christensen

(57) ABSTRACT

There is provided a device arranged to couple electromagnetic radiation into or out of a biological material. The device comprises a first metamaterial comprising: a substrate component having a thickness no greater than a first wavelength of the electromagnetic radiation; and a plurality of elements supported by the substrate component, wherein each element has a first dimension no greater than a first wavelength of the electromagnetic radiation and at least two of the elements of the plurality of elements are non-identical.

32 Claims, 34 Drawing Sheets

(51) Int. Cl.
*G02B 1/00* (2006.01)
*A61B 5/145* (2006.01)
*A61B 5/1455* (2006.01)

(52) U.S. Cl.
CPC ............ *A61B 5/1455* (2013.01); *G02B 1/002* (2013.01); *A61B 2562/143* (2013.01)

(56) References Cited

U.S. PATENT DOCUMENTS

| | | | |
|---|---|---|---|
| 6,801,173 | B2 | 10/2004 | Wiltshire |
| 8,089,038 | B1 | 1/2012 | Latypov |
| 2003/0191376 | A1* | 10/2003 | Samuels ................ A61B 5/00 |
| | | | 600/309 |
| 2004/0140945 | A1 | 7/2004 | Werner |
| 2008/0088524 | A1 | 4/2008 | Bratkovski |
| 2008/0252293 | A1* | 10/2008 | Lagae ................ G01S 13/0209 |
| | | | 324/318 |
| 2009/0206963 | A1* | 8/2009 | Nguyen ............. H03H 9/02417 |
| | | | 334/14 |
| 2010/0078203 | A1 | 4/2010 | Lier |
| 2010/0271692 | A1 | 10/2010 | Hor et al. |
| 2010/0314040 | A1 | 12/2010 | Tyler et al. |
| 2011/0069377 | A1 | 3/2011 | Wu et al. |
| 2011/0260946 | A1* | 10/2011 | Dandekar ............... H01Q 21/28 |
| | | | 343/893 |
| 2011/0317275 | A1 | 12/2011 | Smith |
| 2012/0013989 | A1 | 1/2012 | Choi et al. |
| 2012/0015164 | A1 | 1/2012 | Liu et al. |
| 2012/0049648 | A1* | 3/2012 | Choi ....................... H02J 5/005 |
| | | | 307/104 |
| 2012/0053445 | A1* | 3/2012 | Turnquist ................ A61B 5/01 |
| | | | 600/407 |
| 2012/0075692 | A1 | 3/2012 | Baik et al. |
| 2012/0088982 | A1* | 4/2012 | Rulkov .............. A61B 5/02438 |
| | | | 600/301 |
| 2012/0170114 | A1 | 7/2012 | Domash |
| 2012/0327502 | A1 | 12/2012 | Zheludev et al. |
| 2013/0016030 | A1 | 1/2013 | Liu et al. |
| 2013/0240251 | A1 | 9/2013 | Kaplan et al. |
| 2014/0085693 | A1 | 3/2014 | Mosallaei et al. |
| 2015/0045663 | A1 | 2/2015 | Palikaras et al. |
| 2015/0049487 | A1* | 2/2015 | Connor ............... F21V 33/0008 |
| | | | 362/277 |

FOREIGN PATENT DOCUMENTS

| | | |
|---|---|---|
| EP | 0 694 282 A2 | 1/1996 |
| EP | 1860 458 A1 | 11/2007 |
| EP | 2 688 380 | 1/2017 |
| GB | 762734 | 12/1956 |
| GB | 2 382 230 A | 5/2003 |
| GB | 2 500 719 | 10/2013 |
| JP | 4002982 A | 11/2007 |
| RU | 2 089 166 C1 | 9/1997 |
| WO | WO 2005/053531 A2 | 6/2005 |
| WO | WO 2006/083672 A2 | 8/2006 |
| WO | WO 2012/007147 A1 | 1/2012 |
| WO | WO 2013/054115 A1 | 4/2013 |
| WO | WO 2013/144559 A1 | 10/2013 |

OTHER PUBLICATIONS

Great Britain Search Report for Application No. GB 1403389.8, entitled: Sensor, dated Aug. 27, 2014.

Non-Final Office Action for U.S. Appl. No. 14/389,293, entitled: Electromagnetic Imaging, dated Mar. 30, 2017.

* cited by examiner

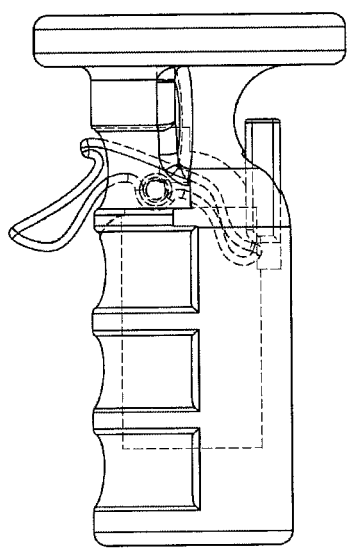
FIGURE 12f
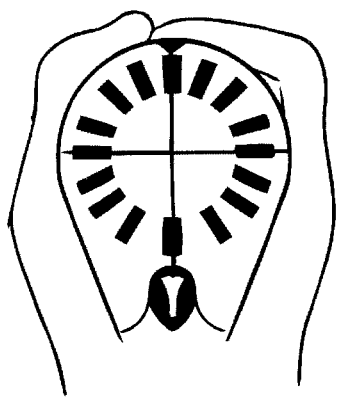
FIGURE 12g
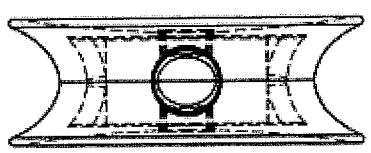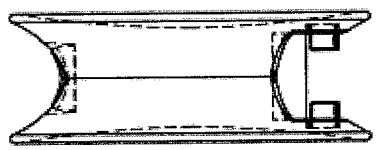
FIGURE 12h
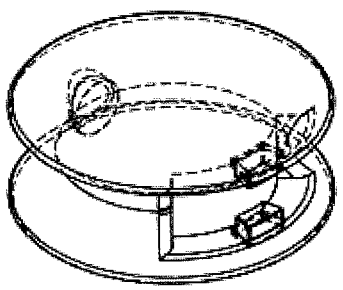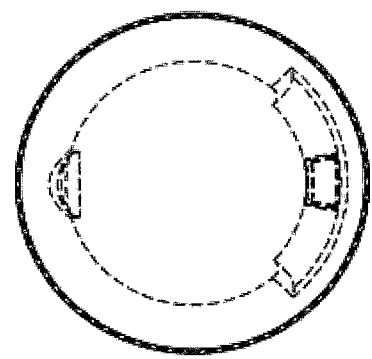

SENSOR

This application is the U.S. National Stage of International Application No. PCT/GB2015/050561, filed Feb. 26, 2015, which designates the U.S., published in English and claims priority under 35 U.S.C. §§ 119 or 365(c) to Great Britain Application No. 1403389.8, filed Feb. 26, 2014. The entire teachings of the above applications are incorporated herein by reference.

FIELD

The present disclosure relates to a device, structure, medium, coating or layer arranged to couple electromagnetic radiation into or out of a biological material, improve the coupling of electromagnetic radiation into or out of a biological sample or increase the coupling of electromagnetic radiation into or out of a biological sample. In particular, the present disclosure relates to a device, structure, medium, coating or layer arranged to reduce reflection. More particularly, the present disclosure relates to an antireflection structure, antireflection layer and an antireflection coating. Further particularly, the present disclosure relates to a metasurface.

BACKGROUND

The most common methods to analyse biological substances include acidity, index of peroxides, UV spectroscopy, thin-layer chromatography, gas chromatography, high performance liquid chromatography, Raman spectroscopy and UV spectroscopy. A drawback of these procedures is that they usually require the isolation and analysis of the components present by procedures that are laborious and time-consuming. It would be advantageous to implement new techniques that with very little or no handling of the sample load produce results similar or superior to those obtained by the established procedures. Furthermore, these methods do not work well for characterizing the inner layers of a biological substance, such as the components of the blood stream which is inside animal bodies. The skin, fat and muscle layers shield the blood from external signals, making their characterization extremely difficult and prone to errors. The same problems are faced when the biological substance is inside an artificial container (bottle or opaque plastic box), as these light-based methods do not offer penetration inside the container.

A different method for characterizing substances (not just biological ones) is dielectric spectroscopy, which utilizes microwaves or radio waves to characterize a sample. In this approach a radio wave signal (usually generated from an antenna) is launched against the sample under test (SUT), and the reflected and transmitted signals are recorded, leading to estimation of the electromagnetic properties of the sample (e.g. its permittivity and permeability), which can then by converted to a material property of the sample (e.g. the percentage of sugar or salt in water, or concentration of bacteria in milk).

Characterizing a biological substance is tremendously advantageous in a particular sector: the concentration of glucose in the human blood (for diabetes patients).

Diabetes is a disease characterized by high glucose levels in the blood (hyperglycaemia). It is the fifth most common cause of mortality worldwide with a global prevalence of 8.3% and 370 million people affected which is set to rise to 550 million by 2030. The cost of diabetes and its associated complications are staggering, estimated to be $130 billion annually in the EU and $245 billion in the USA in 2012 (up from $174 billion in 2007). The burden of uncontrolled diabetes in the long term is substantial as it can lead to a number of secondary complications including; blood vessel damage, cardiovascular disease, kidney failure, neuropathy (nerve damage) and diabetic retinopathy. As these complications progress, they become progressively more expensive to treat.

There is no known cure for diabetes: the condition can only be managed. Diabetes management is primarily focused on accurate measurement of blood glucose levels using glucose meters, enabling tighter control of blood glucose levels by injecting the correct dose of insulin (Type I patients) or taking oral diabetic drugs (Type II). Accurate and timely monitoring of the blood sugar levels is therefore absolutely critical.

There are extensive costs associated with the management and monitoring of diabetes and in the EU diabetes accounts for 10% of the total healthcare budgets. For managing a chronic condition such as diabetes, this proves to be an extremely costly approach. Managing diabetes well at an early stage of the diagnosis helps prevent later, more expensive complications. Better glucose control and management are some of the initiatives that governments are undertaking to reduce the hospital admissions from uncontrolled diabetes. Therefore there is a huge cost benefit to healthcare providers in improving monitoring adherence and accuracy and so preventing the progressive increases in the financial burden associated with diabetes.

A non-invasive glucose monitoring system would have a substantial health impact. First, this would eliminate the need to draw blood from the user to take a glucose reading. This in turn eliminates the pain associated with lancing the finger, need for expensive strips, hygiene and infection issues and risk of contaminating the glucose monitor resulting in potentially fatal incorrect readings. Second, it can provide access to frequent monitoring for those that are not currently fully supported by the healthcare systems, i.e. Type 2 diabetics and pre-diabetics. Finally, such a system is ideal for patients that rely on insulin pumps to control their medication via a built-in feedback functionality that automatically adjusts the pump.

Many non-invasive biomedical applications are based on the interaction or propagation of electromagnetic radiation through biological substances, including the human body. However, fundamental challenges are identified, which arise from the very nature of the microwave field and its interaction with the living tissue. The skin blocks and reflects incident radio waves, which is attributed to the high value of relative permittivity and conductivity of the tissue compared to air. In electromagnetic terms, an impedance mismatch is created. This impedance mismatch, results in degradation of the transmitting energy and reduced accuracy of the applied techniques. This is probably the most critical problem in radio wave propagation for medical purposes. This issue leads to different limitations in major medical applications: for example, in microwave imaging techniques and blood glucose monitoring, the resolution and precision is deteriorated, while in hyperthermia treatments, higher amounts of potentially harmful energy is required.

If this impedance mismatch problem was solved, it would have tremendous impact on the medical applications of radio waves by allowing more accurate devices consuming less power and occupying less space.

Recently, improvements have been made in the area and the inventors' own earlier patent application, GB2500719, discloses a device arranged to improve the coupling of electromagnetic radiation into a target using a metamaterial.

Metamaterials are artificially created materials that can achieve electromagnetic properties that do not occur naturally, such as negative index of refraction or electromagnetic cloaking. While the theoretical properties of metamaterials were first described in the 1960s, in the past 10-15 years there have been significant developments in the design, engineering and fabrication of such materials. A metamaterial typically consists of a multitude of unit cells, i.e. multiple individual elements (sometimes refer to as "meta-atoms") that each has a size smaller, typically much smaller, than the wavelength of operation. It may be said that each element has at least one "sub-wavelength" dimension. These unit cells are microscopically built from conventional materials such as metals, plastics and dielectrics. However, their exact shape, geometry, size, orientation and arrangement can macroscopically affect radiation in an unconventional manner, such as creating resonances or unusual values for the macroscopic permittivity and permeability.

Some examples of available metamaterials are negative index metamaterials, chiral metamaterials, plasmonic metamaterials, photonic metamaterials, etc. Due to their sub wavelength nature, metamaterials that operate at microwave frequencies have a typical unit cell size of a few millimetres, while metamaterials operating at the visible part of the spectrum have a typical unit cell size of a few nanometres. Metamaterials can strongly absorb radiation at certain narrow range of frequencies.

For conventional materials, the electromagnetic parameters such as magnetic permeability and electric permittivity arise from the response of the atoms or molecules that make up the material to an electromagnetic wave being passed through. In the case of metamaterials, these electromagnetic properties are not determined at an atomic or molecular level. Instead these properties are determined by the selection and configuration of a collection of smaller objects, such as conducting components or elements that make up the metamaterial. Although such a collection of objects and their structure do not "look" at an atomic level like a conventional material, a metamaterial can nonetheless be designed so that an electromagnetic wave will pass through as if it were passing through a conventional material. Furthermore, because the properties of the metamaterial can be determined from the composition and structure of such small objects, the electromagnetic properties of the metamaterial such as permittivity and permeability can be accurately tuned on a very small scale.

GB2500719 discloses the use of a metamaterial comprising a periodic array of unit cells. Notably, the unit cell is regular and the array is regular. The present disclosure sets out a further improvement made by the inventors.

SUMMARY

Aspects of the present disclosure are defined in the appended independent claims.

In summary, there is provided a device for coupling electromagnetic radiation into or out of a biological material. The device comprises a metamaterial wherein at least two of the meta-atom elements are unlike. In particular, the size and/or shape of the metamaterial elements differ. Optionally, at least some of the metamaterial elements are asymmetric or comprise only one axis of symmetry. Optionally, the array of metamaterial elements is irregular. The dimensions of the component elements are optimised for the application. There is also provided a sensor comprising two coupling devices.

The elements of the metamaterial are arranged to affect the amplitude and/or phase of the electromagnetic radiation. The elements of the metamaterial in accordance with this disclosure are not designed to provide significant energy storage. By tuning the size, shape, dimensions and positioning of the component elements, reflectivity may be reduced. The reflectivity may be caused by a containing component such as skin or a bottle. Other effects may be imparted on the electromagnetic radiation such as wave focusing.

BRIEF DESCRIPTION OF THE DRAWINGS

Embodiments of the present disclosure will now be described with reference to the accompanying drawings in which:

FIGS. 12a to 12m show some design configurations;

In the figures, like reference numerals refer to like parts.

DETAILED DESCRIPTION OF THE DRAWINGS

Embodiments refer to "biological material" which is a material that is typically either plant material, animal material, or some other substance that can be found in a life form. Some examples include human tissue (hand, skin, muscle, ear, etc.), animal tissue (e.g. from a mouse, cow or pig), water, blood, milk, saliva, tears, urine, carbonated drinks, and fruit juice, wine, and oil. However, it may be understood that the present disclosure is equally applicable to any biological sample.

Embodiments refer to "irregular" shapes which include shapes having no axis of symmetry and shapes having only one axis of symmetry.

A metamaterial comprises a substrate component having a thickness no greater than a first wavelength of the electromagnetic radiation; and a plurality of elements supported by the substrate component, wherein each element has a first dimension no greater than a first wavelength of the electromagnetic radiation. Embodiments refer to a "metasurface" which may be considered a special type of metamaterial. Specifically, a metasurface is a metamaterial in which at least two of the elements of the plurality of elements are non-identical, or different, in any one or more of size, shape, orientation and composition. A metasurface is only two-dimensional.

Device for Coupling Electromagnetic Radiation

In overview, the present disclosure describes use of certain types of metamaterials to enhance radio wave penetration through the skin and, therefore, solve the mismatch problem. This is achieved by harnessing the novel and special electromagnetic properties of a subset of metamaterials.

Conventionally, metamaterials comprise unit cells arranged in periodic patterns. However, the inventors have recognised that a specific type of metamaterial, sometimes called a "metasurface", is particularly advantageous for coupling electromagnetic radiation into biological samples particularly biological samples in a container.

Metasurfaces are easy to fabricate and offer the opportunity to build low-loss structures. The properties of the metasurface are determined from the periodicity and the design of their constituent elements. Note that, unlike other metamaterials, which are periodic arrangements of the same element, a metasurface usually comprises of different elements. Likewise, the elements of a metasurface are not necessarily periodically arranged. The present disclosure relates to a metamaterial in which at least two of the sub-wavelength elements of the plurality of elements are different in shape and/or size and/or composition and/or orientation.

Figure 1:
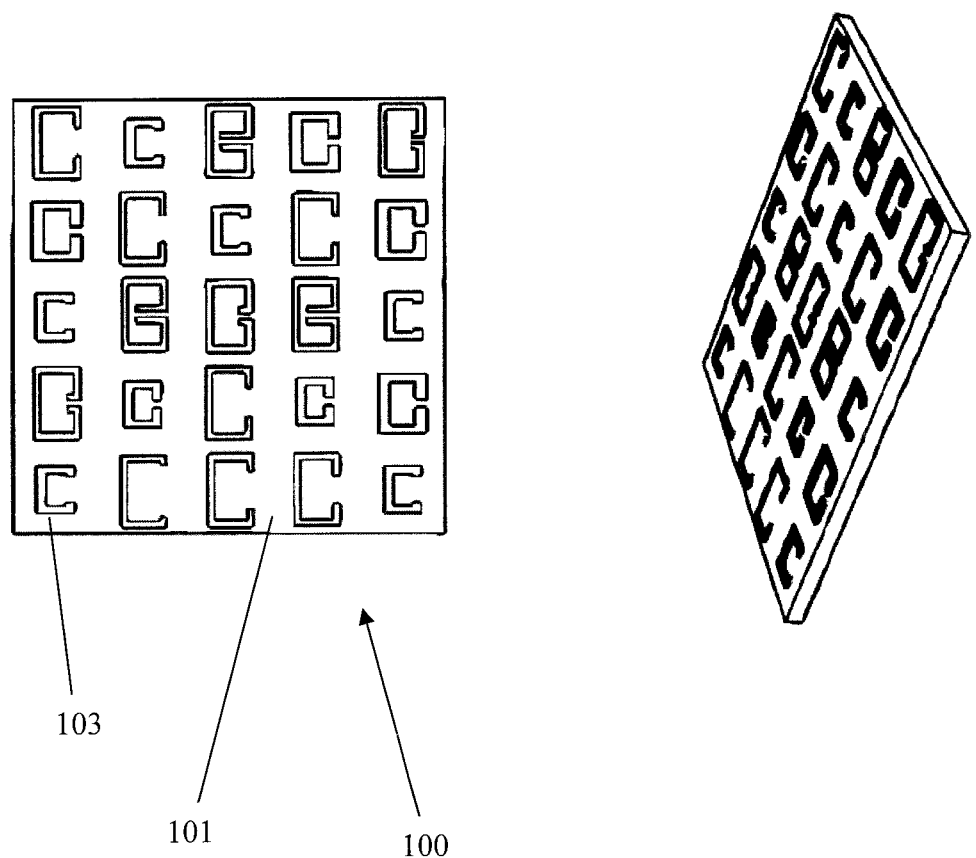
FIG. 1 is a metasurface having a periodic pattern.

FIG. 1 shows a metasurface 100, in accordance with the present disclosure, comprising a substrate component 101 and a plurality of elements 103. As shown in FIG. 1, elements 103 differ in size and shape. However, in this embodiment, elements 103 are arranged in a substantially regular array. That is, the spacing between the centres of adjacent elements is substantially constant in two orthogonal directions.

There is therefore provided a device arranged to couple electromagnetic radiation, the device comprising a first metamaterial comprising: a substrate component having a thickness no greater than a first wavelength of the electromagnetic radiation; and a plurality of elements supported by the substrate component, wherein each element has a first dimension no greater than a first wavelength of the electromagnetic radiation and at least two of the elements of the plurality of elements are non-identical.

Advantageously, the inventors have found that using a metasurface significantly reduces the losses associated with resonances occurring in conventional metamaterials. In fact, it is found that a nearly loss-less system can be produced using a metamaterial wherein at least two of the elements of the plurality of elements are non-identical. Further advantageously, this type of metamaterial is very thin and easy to fabricate. This makes it even more preferable as a sensor for biological materials particularly biological materials in a container. In particular, it makes the device particularly suitable as an antireflective component such as an antireflection coating. These advantageous are achieved because impedance matching and/or shaping of the electromagnetic radiation can be achieved when differing size and/or shape elements are used.

In an embodiment, the first dimension is the direction for propagation of the electromagnetic radiation. In embodiments, the first dimension is the thickness of each element. Accordingly, the elements are not designed to provide substantial energy storage which requires greater volume. In embodiments, all dimensions of each element are less than the wavelength of the electromagnetic radiation. In embodiments, the first wavelength comprises a bandwidth of wavelengths including the first wavelength.

Some of the elements 103 shown in FIG. 1 may be considered irregular and/or asymmetric. That is, in an embodiment, at least one of the elements of the plurality of elements has an irregular shape. In an embodiment, all the elements of the plurality of elements have an irregular shape. Advantageously, this allows for finer tuning of the characteristics of metasurface, because more degrees of freedom are available in the tuning of its performance.

In an embodiment, the biological material is bound by a container. In embodiments, the biological material is enclosed by the container. In an embodiment wherein the biological material is blood, the container includes skin. In an embodiment wherein the biological material is food stuff, the container is a plastic bottle. Further examples are given below.

Figure 2:
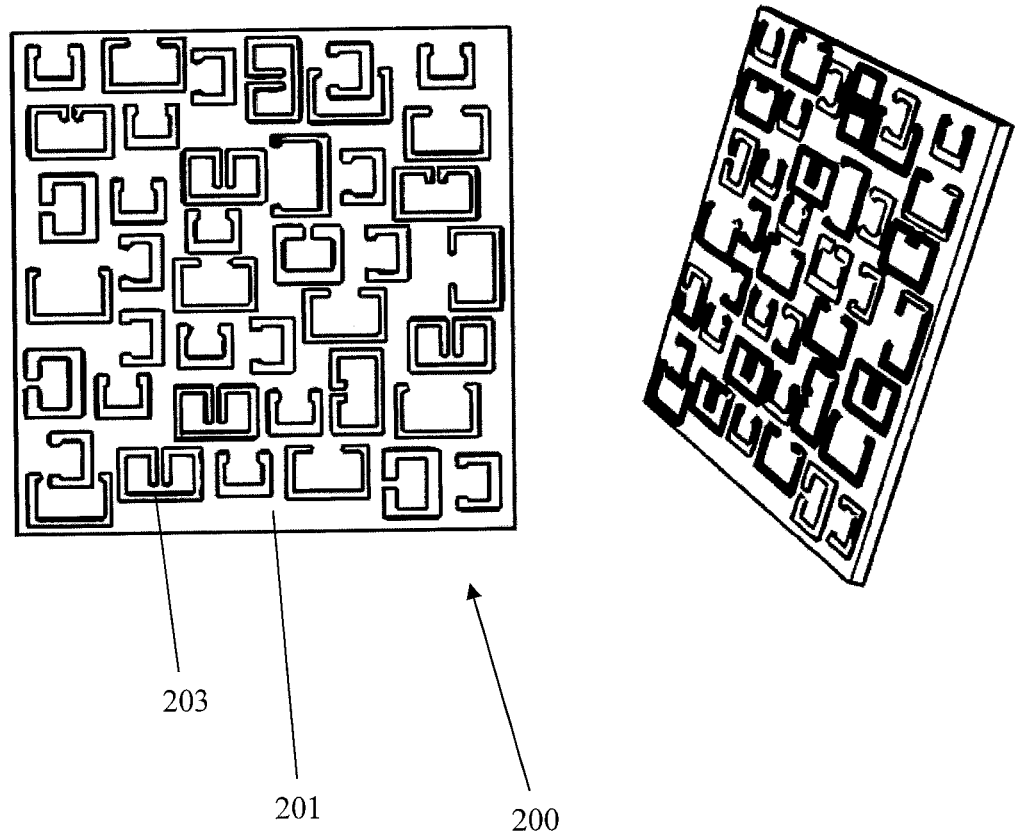
FIG. 2 is a metasurface having a non-periodic pattern.

FIG. 2 shows an embodiment in which the elements are arranged in a non-periodic pattern. FIG. 2 shows a metasurface 200 comprises a substrate component 201 and a plurality of irregularly positioned elements 203. The elements 203 are also irregular in size and shape. It is not essential that all elements in the array of elements are irregularly arranged. In embodiment, at least a subset of the elements is arranged in an irregular array. In a further embodiment, all the elements are arranged in an irregular array. Advantageously, irregularity in the positioning of the elements allows for finer tuning of the characteristics of metasurface.

Figure 3:
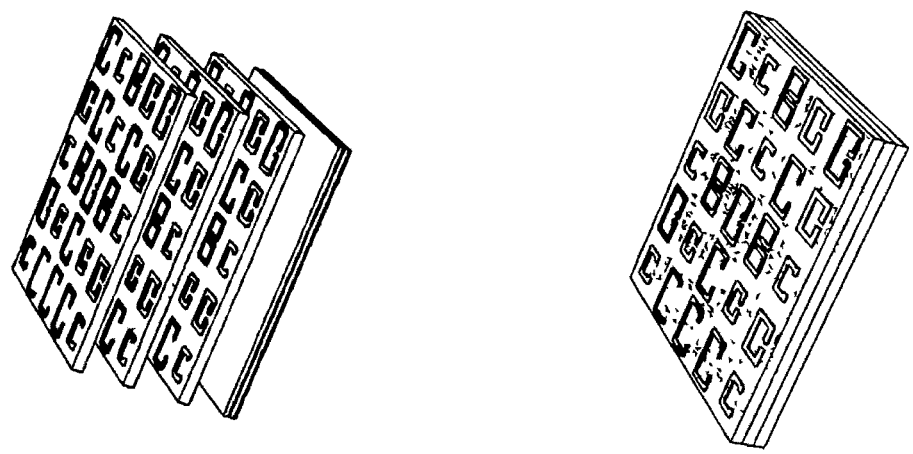
FIG. 3 shows multiple metasurface layers in a periodic configuration.
Figure 4:
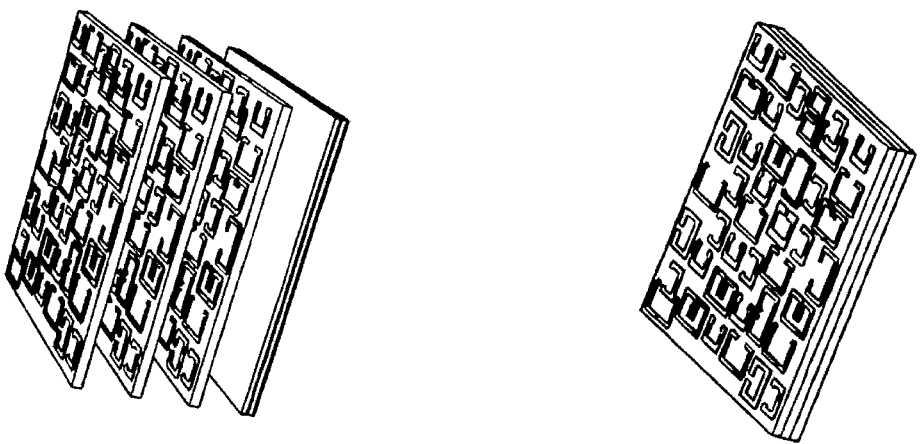
FIG. 4 shows multiple metasurface layers in a non-periodic configuration.

The metasurfaces shown in FIGS. 2 and 3 are substantially planar. That is, in an embodiment, the substrate component is planar. The metasurface is designed for electromagnetic radiation to pass through in a direction perpendicular to the plane of the metasurface. In other embodiments, the metasurface is non-planar or curved such as spherical or cylindrical. In embodiments, the substrate is flexible. Losses associated with transmission through the metasurface are reduced because the electromagnetic radiation passes through a smaller volume of metamaterial.

In an embodiment, the substrate component is a dielectric and the elements are conducting. In an embodiment, the elements are formed from any conducting material including homogeneous materials such as metals as well as composites and nanocomposites including Bragg reflectors. The elements may be formed, for example, from silver, gold, copper and/or aluminium, or any other metal that supports reflections at the wavelength of interest.

The skilled person will understand that any suitable technique for producing the conducting component on a dielectric support structure may be appropriate. In embodiments, etching, photoresist etching, e-printing or lithographic techniques are used. In other embodiments, a self-assembly chemical process is used.

In an alternative embodiment, the substrate component is conducting and the elements are a dielectric.

The thickness of the elements may be few micrometres to a few centimetres. At least one dimension of the elements is sub-wavelength.

The "sub-wavelength" periodic arrangement of metallic and dielectric elements allows the periodic conducing component to resonate at a resonant frequency (or wavelength). The skilled person will understand that there may be a narrow band of frequencies centred on the resonant frequency at which at least partial resonance will occur. At the resonant frequency, radiation will be at least partially "captured" by the metamaterial and amplification may occur by constructive interference, for example. The metamaterial forms a type of waveguide in which the fields inside the "waveguide" are bound and contained, permitting amplification. Accordingly, there is provided a device arranged to increase the penetration of radiation into a target.

In embodiments, the device is tuned to the source and target medium. It is found that an incident wave travels along the path of least resistance of the conducting component of the metamaterial. For example, if source provides a plane wave of radiation, symmetric conducting elements may be preferred. The shape and configuration of the conducting may also be chosen to match the polarisation of the incident radiation. For example, conducting elements having horizontal and vertical features may be preferred for horizontally and vertically polarised radiation.

The conducting elements may comprise features having a length optimised for a wavelength of interest. In embodiments, the length of a primary feature is approximately half the wavelength of the incident radiation. For example, a conducting component having a long element, such as a spiral or a regular meander, will have a relatively long resonant wavelength. For example, the number of turns in the spiral of regular meander may be increased to increase the resonant wavelength. The conducting elements may comprise a sense of rotation such as a left-handed or right-handed spiral optimised for circularly or elliptically polarised radiation, for example. The shape and dimension of the elements may be optimised experimentally or numerically.

In embodiments, optimization of the shape of the elements is achieved via numerical simulation such that the device enhances the penetration of waves at a particular wavelength. The shape of the elements can also be optimised to modify the amplitude and phase of the incident wave in a way that the output wave has particular properties, such as maximized transmission, or a phase front result in a focusing wave, or a wave with a specific polarisation (e.g. linear or right hand circular). In one embodiment, there is designed a model of the system in an electromagnetic simulator. The model includes all the components of the system: the source medium, the device component or components, the target medium, and any other features embedded in the target medium that needs to be imaged. Then the electromagnetic properties as a function of frequency of each component are specified, such as the electric permittivity, permeability, conductivity or loss. Then the S-parameters (reflection and transmission) of the system are evaluated as a function of frequency. The frequency range where the transmission is maximized may indicate the optimal operational range of the system. In other embodiments, the aim is not to maximise transmission but to form a transmitted wave having a particular phase and amplitude at each location behind each metasurface element. For example, the phase may be changed linearly along the metasurface elements to form an output wave which propagates at an angle compared to the incident one. When the geometry of the elements is modified, the transmission peak will be varied accordingly. Thus one can modify the shapes (or their period) to tune the operational frequency to the frequency or frequencies of interest (e.g. the radiation frequencies of the antenna system that generates the incident waves).

An operational principle of the metamaterial is that it is highly resonant around specific frequencies. For those frequencies, the wave transmission through the array is enhanced multiple times and thus increased wave penetration through the target occurs. That is, the plurality of elements are collectively arranged to resonate at a first wavelength of the electromagnetic radiation. The resonance condition is determined by the geometry of the array elements, and is optimized for transmission when it is placed on top of a particular target. That is, the components of the device are tailored to the target.

Each element of the plurality of elements may be individually tuned to the source, container and biological material. To design a metasurface in accordance with the present disclosure, it may be modelled as a transmission line element. For example, the metasurface can act as a matching stub between the two media, and its impedance can be designed such that the desired transmission from one medium to another is optimized. The transmission coefficients are related to the sheet impedances using analytical modelling. Then, the impedance of the metasurface will determine the custom design of the unit element (e.g. tested with simulation software), which, when combined in a pattern will create the metasurface with the necessary response at the frequency of interest to allow the high transmission of incident radiation with minor reflections.

In embodiments, metasurfaces are designed and used specifically to interact with human tissue on the transmitted side. The metasurface is specifically designed to 1) maximize the transmission through the tissue or biological sample, and/or 2) focus the incident energy in a particular spot inside the receiving sample. This can be achieved by optimizing the shape of the metasurface elements based on the desired phase that should be imparted on the incident wave.

The transmission line theory implies that the metasurface can act as a matching stub between the air and the skin tissue. By knowing the characteristics of air and skin, the transmission and reflection coefficients can be derived and related to the sheet impedance of the metasurface. These impedance characteristics will determine the custom design of the subwavelength unit element, which microscopically will "manipulate" the incident wave and provide the necessary reactance for the impedance matching. This custom design is obtained performing some numerical calculations using a numerical computing environment. After this modelling, the calculated structures are evaluated and optimized using electromagnetic evaluation software.

The substrate serves as a support structure for the shaped elements. In embodiments, the shaped elements are coated on the surface of the substrate. In other embodiments, the shaped elements are embedded within the substrate. The skilled person will understand that the array of shaped elements may be supported on the substrate in a variety of ways. In embodiments, the substrate is flexible. In embodiments, the device is a multilayer device comprising a plurality metallic-comprising layers and/or dielectric-comprising layers.

Metasurface Design Example

The following is an example of how to design a metasurface array.

The purpose of the metasurface is to impose a specific phase and amplitude change along an incident wave. The properties of the metasurface are extracted by the ratio of the desired electric and magnetic field before and after the metasurface The first step to design the metasurface is to determine the necessary sheet impedances at the operating frequency.

$$Y_{es} = \frac{2(H_1^z - H_2^z)}{E_1^y - E_2^y} \quad (1.1)$$

$$Z_{ms} = \frac{2(E_1^y - E_2^y)}{H_1^z - H_2^z} \quad (1.2)$$

Here $Y_{es}$ and $Z_{ms}$ are the sheet admittances and impedances of the metasurface (which are a function of frequency and position). H and E are the electric and magnetic fields around the metasurface: the superscripts (y or z) indicate the vector field components, while the subscripts indicate the position before (index=1) or after (index=2) the metasurface. In this example the wave propagates along the x-direction, and the metasurface is located in the y-z plane.

This example relates to the design of a metasurface to refract an incident plane wave originating from air into a 45 degree angle at a 60 GHz frequency. It can alternatively be designed to focus the wave at a particular spot inside the target medium (e.g. biological material) on the transmission side, or exactly match the impedance (maximize transmission). The important factor is the ratio of the desired electric and magnetic fields exactly before and immediately after the metasurface elements.

Figure 5:
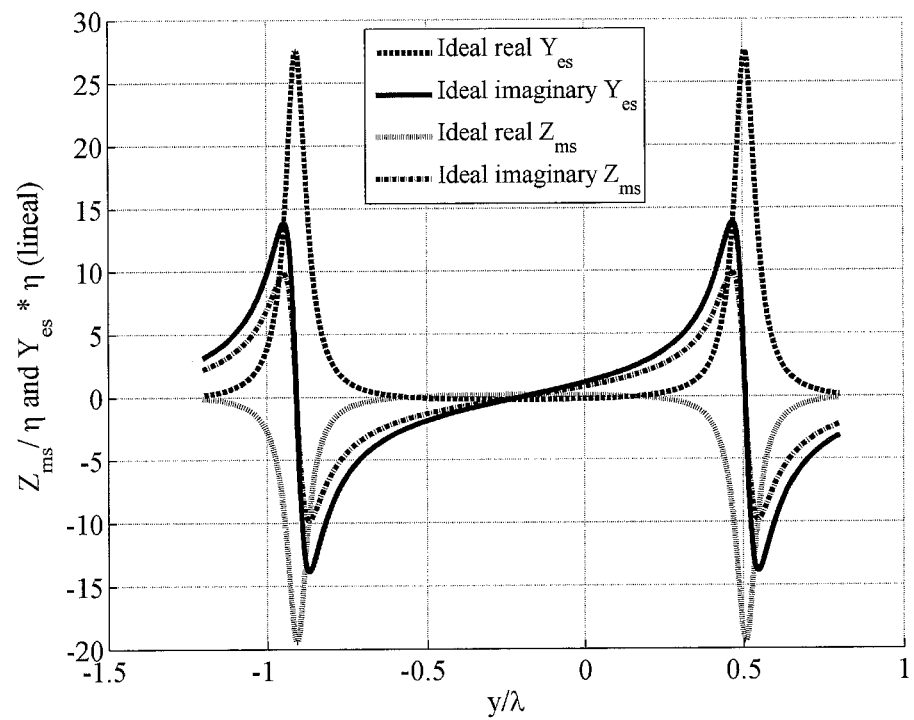
FIG. 5 shows real and imaginary sheet impedances to refract a normally incident electromagnetic wave to an angle of 45 degrees.

The results obtained after calculating the fields along the metasurface length (perpendicular to the direction of propagation) are shown in FIG. 5.

In FIG. 5, periodicity is shown. This periodicity will lead to a periodic metasurface, which will be subdivided in individual unit cells. A typical number is between 5-20 elements for each period along the y axis, although more (smaller) elements can be used to increase the resolution.

Once the sheet impedances are known, it is possible to extract the values of the reflection and transmission coefficients using equations 1.3 and 1.4.

$$T = \frac{\eta(4 - Y_{es} Z_{ms})}{(2 + \eta Y_{es})(2\eta + Z_{ms})} \quad (1.3)$$

$$R = \frac{2}{2 + \eta Y_{es}} - \frac{2}{2\eta + Z_{ms}} \quad (1.4)$$

Figure 6:
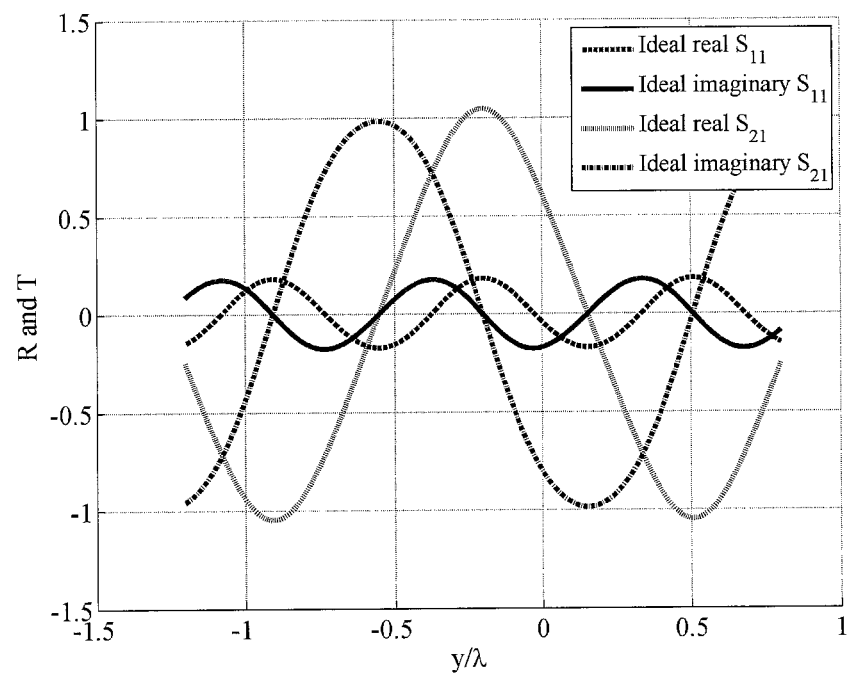
FIG. 6 shows reflection and transmission coefficients derived from the sheet impedances of FIG. 5.

Here η is the wave impedance of the background medium. FIG. 6 shows the reflection and transmission coefficients derived from the sheet impedances of FIG. 5.

The metasurface in accordance with the present disclosure is made of different unit cells, the study will focus on designing one of them. In an embodiment, to start the design, one of the unit cells is deliberately "tuned out". In this example each metasurface element consists of two sub-elements on either side of a dielectric substrate (e.g. Teflon).

Figure 7:
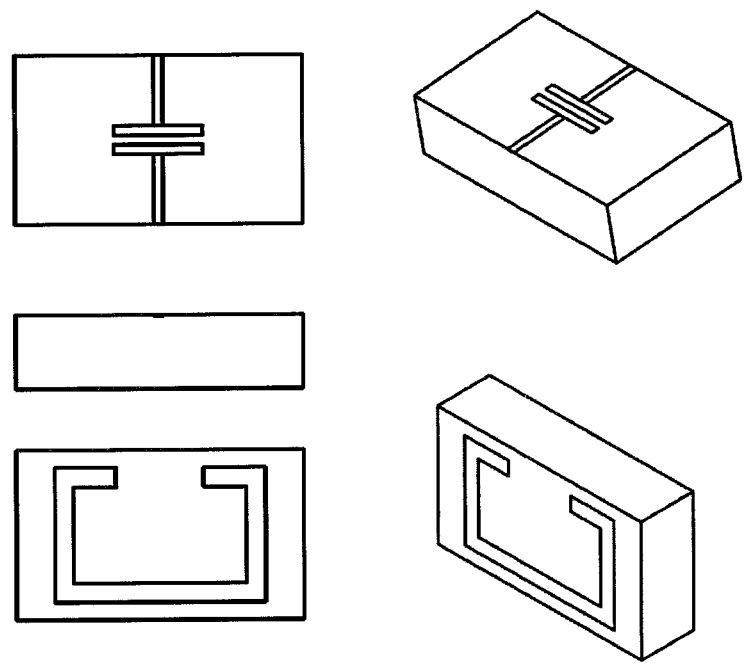
FIG. 7 illustrates various views of the metasurface element of the design example.

FIG. 7 shows various views of a metasurface element in accordance with this example.

The goal is to obtain S-parameters in accordance with equation 1.5 in order to achieve the correct performance for this block.

$$S_{11} = -0.1327 + 0.1107i \quad S_{21} = -0.3290 - 0.9360i \quad (1.5)$$

Figure 8:
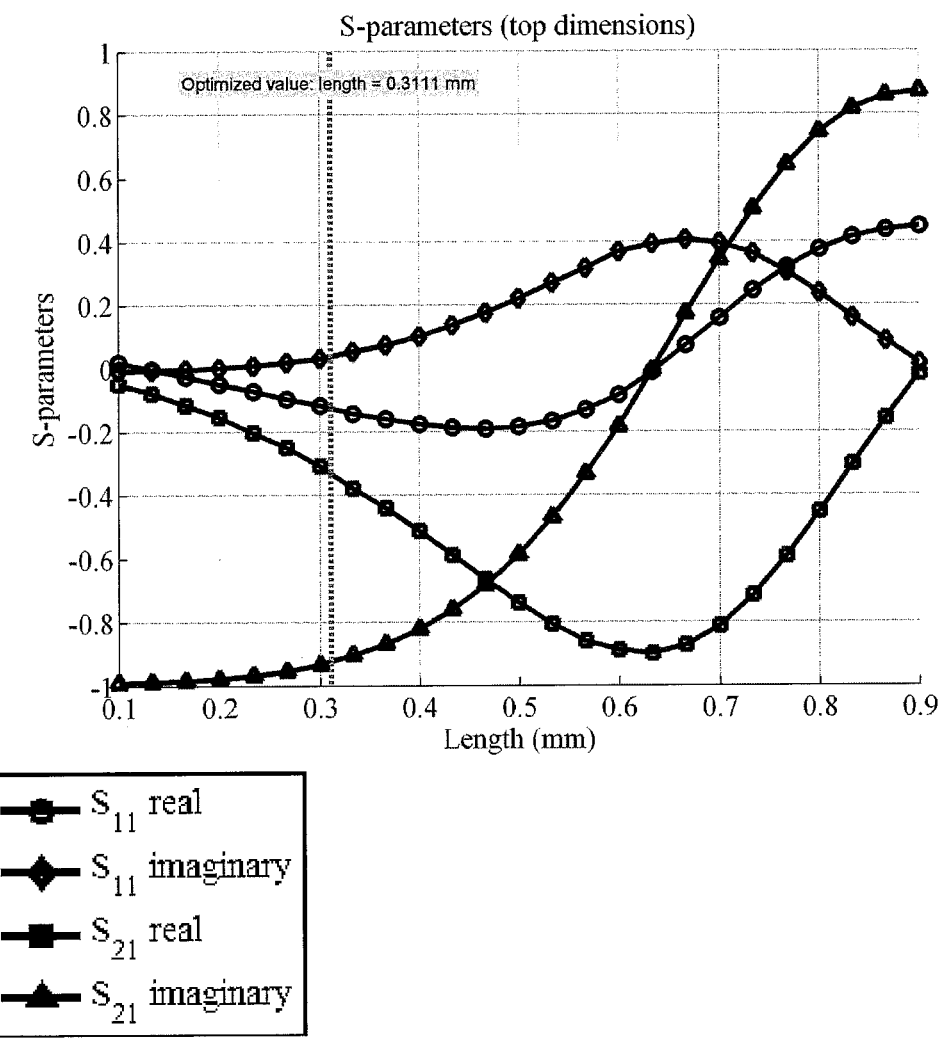
FIG. 8 plots S-parameters obtained changing the length of the parallel copper bars of the top metasurface component of the design example.

FIG. 8 shows the obtained simulated S-parameters of the metasurface element as the length of the rods in the top element and the gap in the ring in the bottom element is varied.

Figure 9:
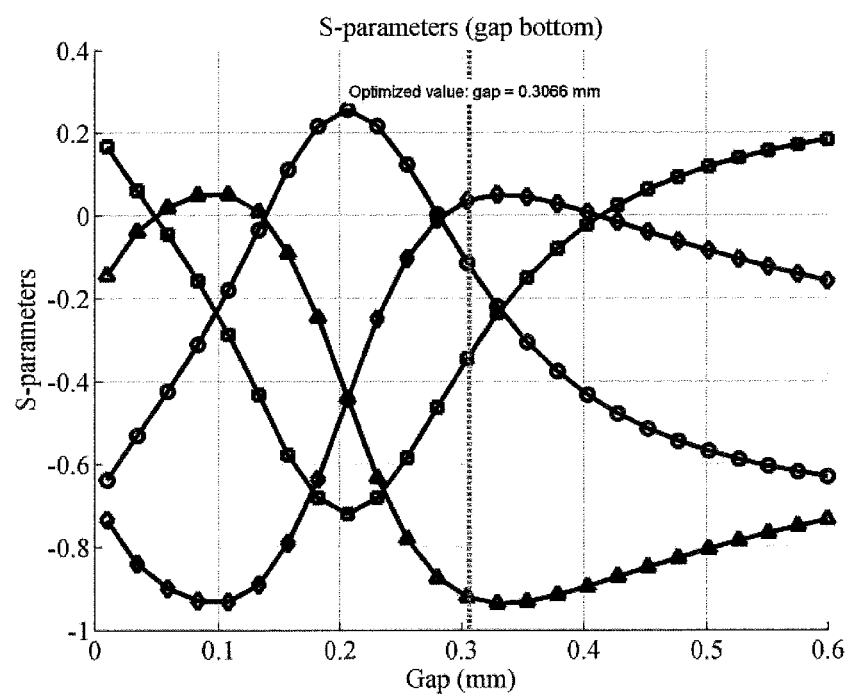
FIG. 9 plots S-parameters obtained changing the gap of the metal ring of the bottom metasurface element.

FIG. 9 shows the S-parameters obtained changing the gap of the metal ring of the bottom metasurface element.

From this, it is possible to make a first approximation to the solution. However, to obtain the most accurate values, it is necessary to do an optimization. This optimization may be performed, for example, in simulation software.

Figure 10:
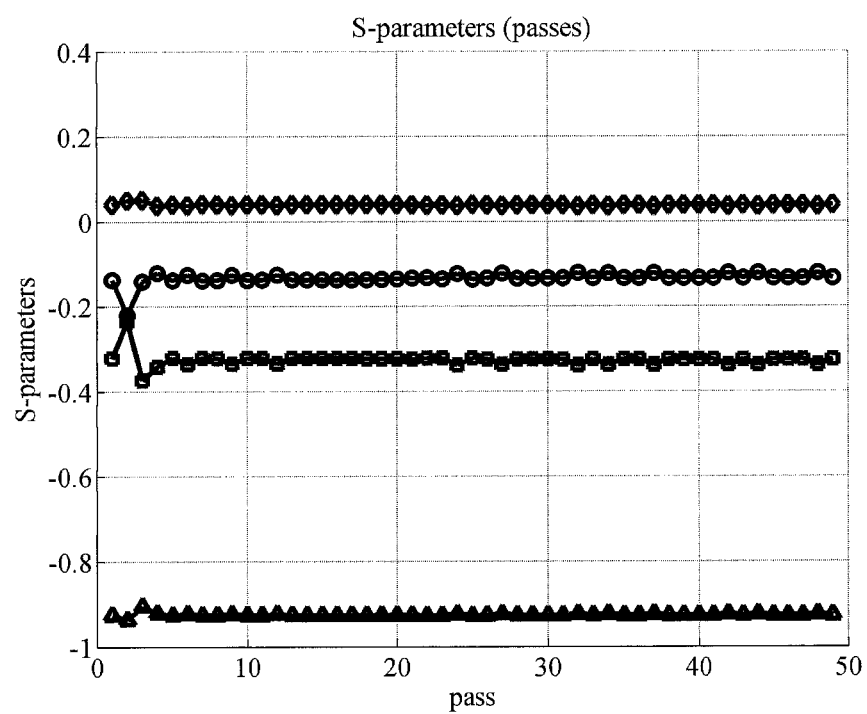
FIG. 10 shows optimisation progress for the metamaterial element dimensions.

FIG. 10 shows optimisation progress for the metasurface elements dimensions.

After optimization, the resulting S-parameters are:

$$S_{11} = -0.1327 + 0.03968i \quad S_{21} = -0.3245 - 0.9261i \quad (1.6)$$

Figure 11A:
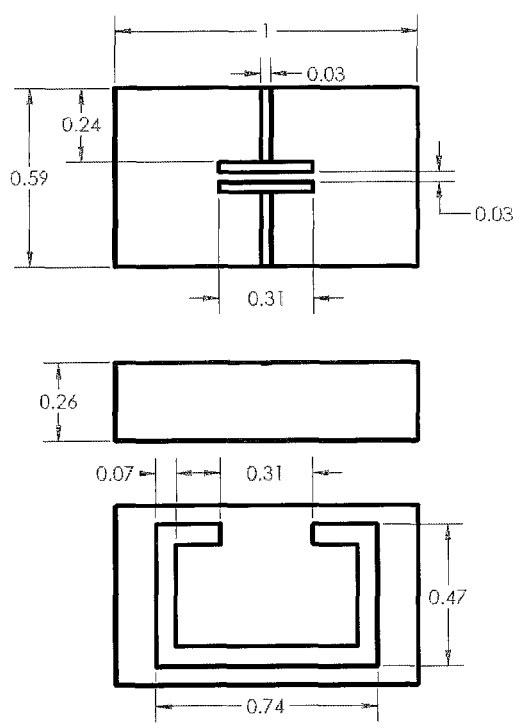
FIG. 11a shows the optimised geometry characteristics for the metasurface element at 60 GHz.

The optimized metasurface element is shown in FIG. 11a. The optimised S-parameters are indicated with vertical lines in FIGS. 8 and 9. In embodiments, each metasurface element is generally or substantially cross-shaped.

Each metasurface element can be designed in a similar fashion.

Figure 11B:
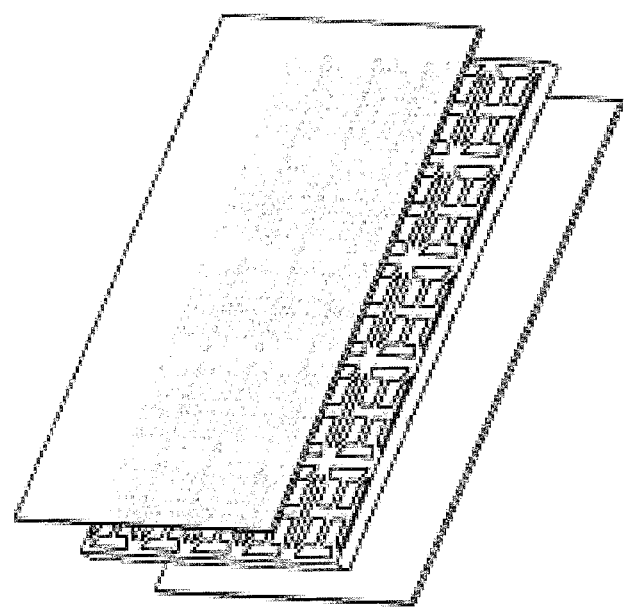
FIG. 11b is a metasurface structure in accordance with embodiments.
Figure 11C:
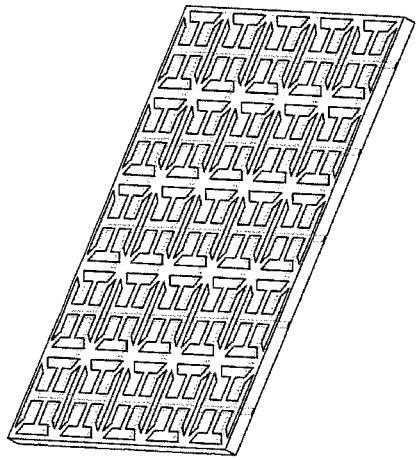
FIGS. 11c, 11d and 11e are further views of a metasurface structure in accordance with embodiments.
Figure 11D:
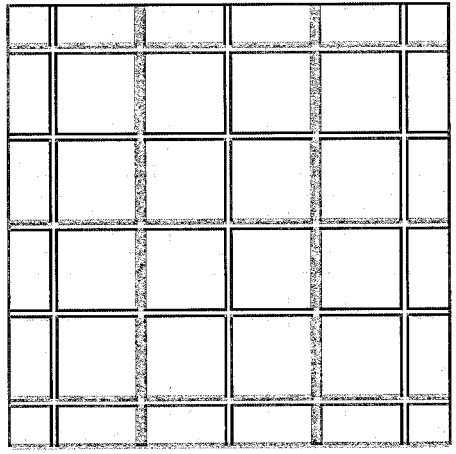
Figure 11E:
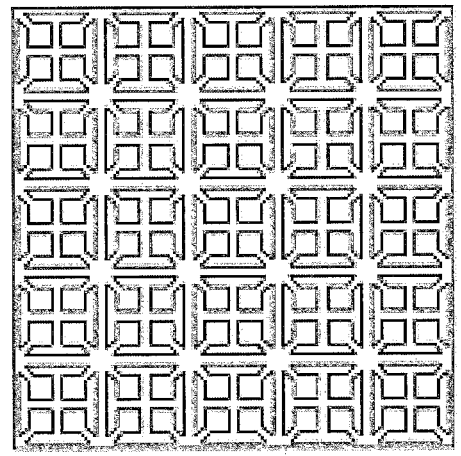

In an embodiment, there is provided a metasurface which comprises a combination of metallic crosses and so-called Jerusalem crosses separated by a dielectric substrate. In embodiments, the dielectric substrate is a liquid crystal polymer. FIG. 11b shows an exploded view of an embodiment comprising two metallic patterned layers separated by a dielectric and sandwiched between two dielectric layers (5 layers total). FIG. 11c is a schematic of the bare metasurface structure (two metallic patterns on either side of a dielectric). In embodiments, the metallic parts are embedded into the dielectric. In other embodiments, the metallic parts protrude the dielectric. FIGS. 11d and 11e show top and bottom views of the metallic layers.

In embodiments, the metasurface elements are optimised to induce convergence of the near-field. These "near-field focusing structures" can lead to focusing details of size well below the diffraction limit. Accordingly, the metasurface may be designed to provide focusing inside a sample—for example, a biological sample in a container. In conventional materials, focusing is usually achieved by properly shaping a homogenous material (e.g. glass), producing lens-type structures. With metasurfaces in accordance with the present disclosure, the shape of the structure can remain flat, but it is no longer homogenous, as it consists of different metallic and dielectric elements.

Additional Layers

The device may comprise a plurality of metasurfaces wherein each metasurface is tuned differently. For example, each metasurface may be arranged to resonate at a different wavelength. In embodiments, by at least partially overlapping the resonant wavelengths of a plurality of metasurfaces, a pseudo-broadband device is formed. For a pseudo-broadband device, the resonant frequency of adjacent layers may differ by an integer multiple of a half wavelength, for example.

In an embodiment, the device further comprising a second metamaterial coupled to the first metamaterial, wherein the second metamaterial comprises: a substrate component having a thickness no greater than a second wavelength of the electromagnetic radiation; and a plurality of elements supported by the substrate component, wherein each element has a first dimension no greater than a second wavelength of the electromagnetic radiation and at least two of the elements of the plurality of elements are non-identical.

In an embodiment, the second metamaterial is arranged, in cooperation with the first metamaterial, to resonate at a second wavelength of the electromagnetic radiation.

In an embodiment, the first wavelength is different to the second wavelength. In embodiments, the second wavelength also comprises a bandwidth of wavelengths including the second wavelength.

In embodiments, there is provided an additional near-field focusing component which is dedicated to providing the near-field focusing described above. In embodiments, the near-field focusing component is placed immediately adjacent the device for coupling EM radiation in accordance with the present disclosure. In an embodiment, the near-field focusing component is a 22 mm by 22 mm by 0.368 mm structure, made up of smaller square unit cells with a period of 2 mm. The unit cell comprises three layers of metallic elements separated by dielectric layers. Unit cells with a large range of transmission ($S_{21}$) phases are required for the lens. Numerical simulation may be used to find suitable designs by varying parameters to affect the $S_{21}$ phase and magnitude. The inventors found that single elements did not provide larger phase ranges and so, in embodiments, the near-field focusing component comprises multiple layers of elements. In embodiments using a three-layer design, the inventors found that it was possible to keep the total transmission high: all unit cells chosen had a $S_{21}$ magnitude greater than 0.8. Unit cells with three layers of elements, produced a 360° $S_{21}$ phase range. In embodiments, the outer two elements are rectangular bars and the inner elements are split ring commutators. The target focal length was 18 mm.

Figure 11F:
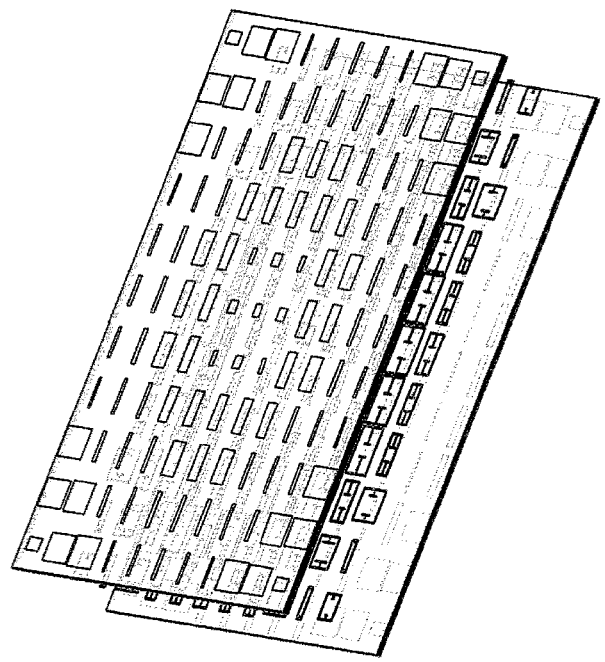
FIGS. 11f, 11g and 11h show an example of a planar near-field focusing component.
Figure 11G:
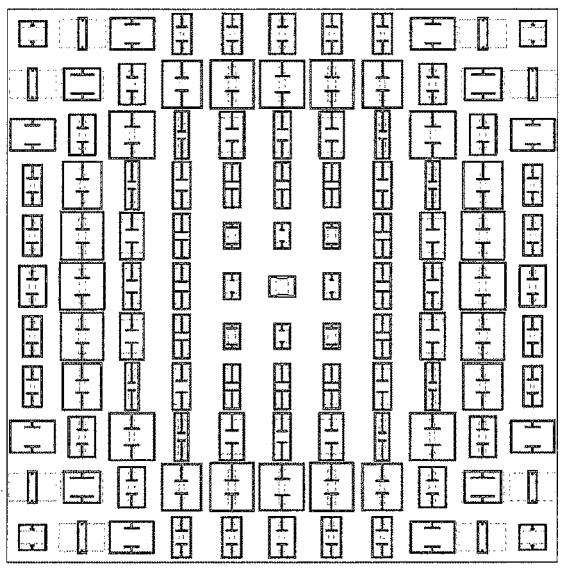
Figure 11H:
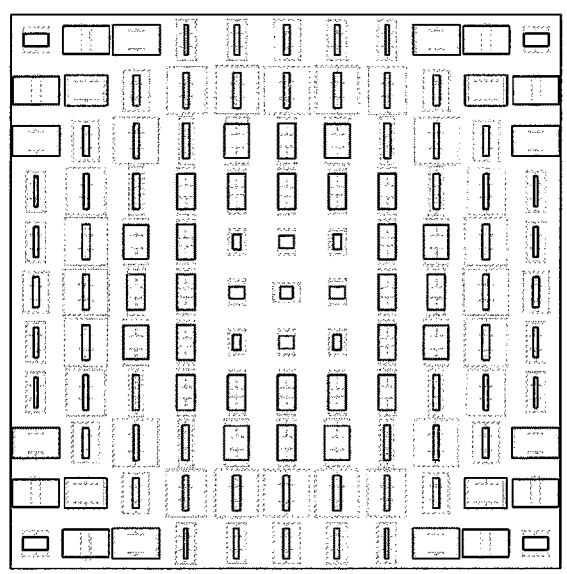
Figure 11I:
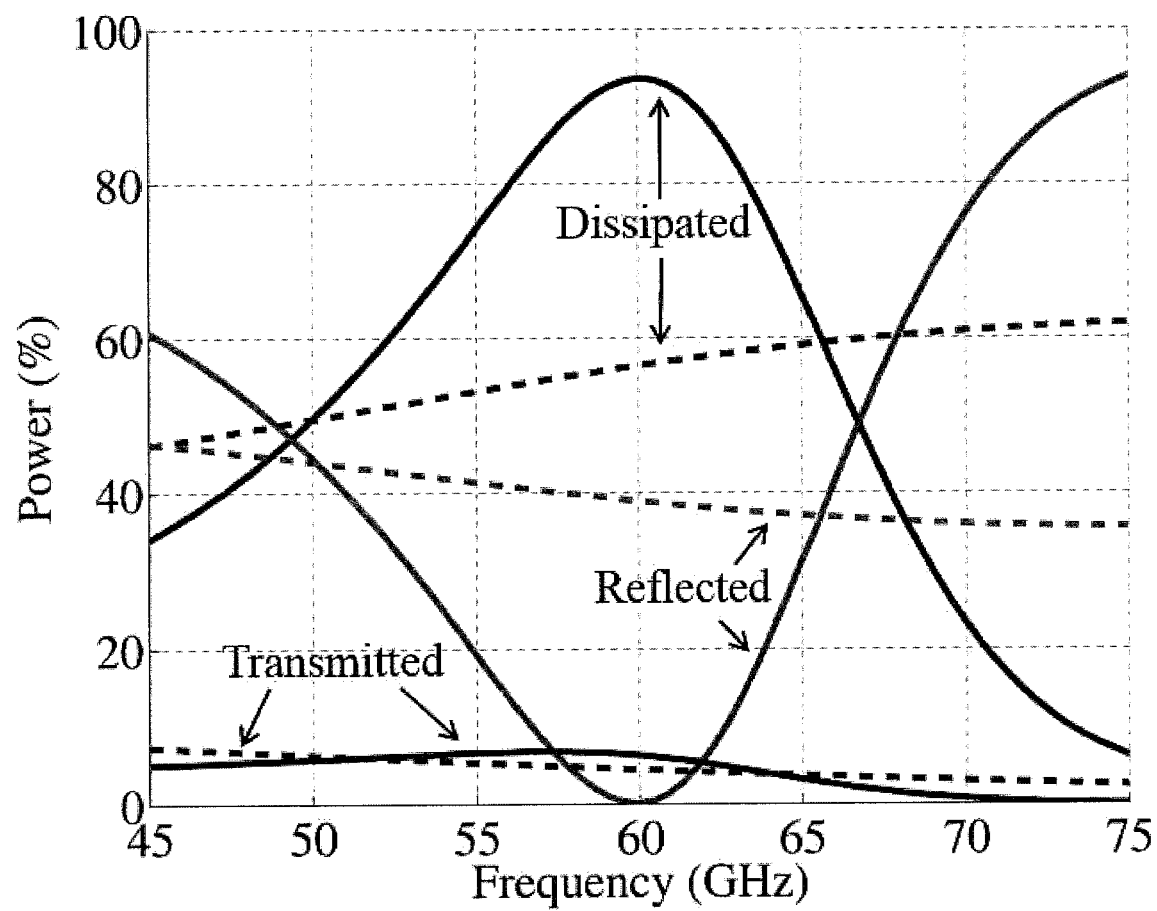
FIG. 11i shows a simulation result of the power penetration in the case when the metasurface in accordance with the present disclosure is placed against human skin.
Figure 12A:
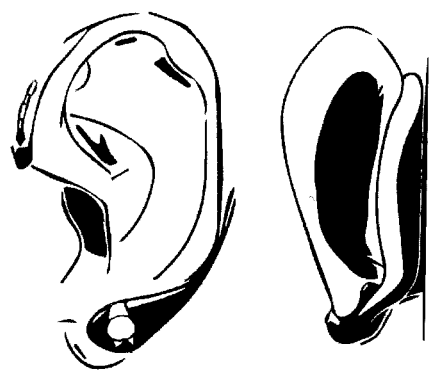
Figure 12B:
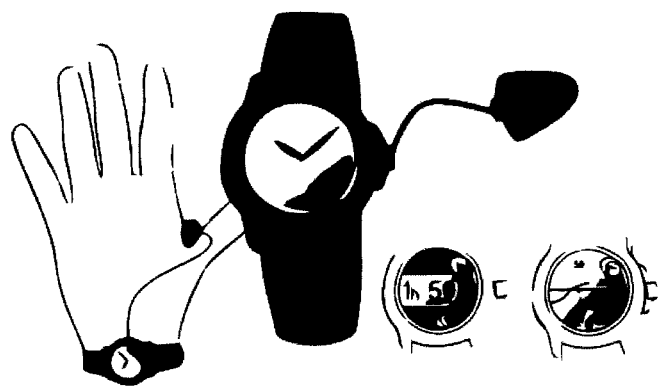
Figure 12C:
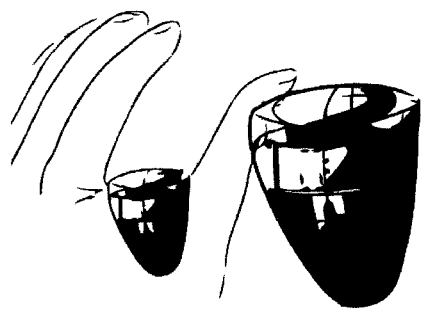
Figure 12D:
Figure 12E:
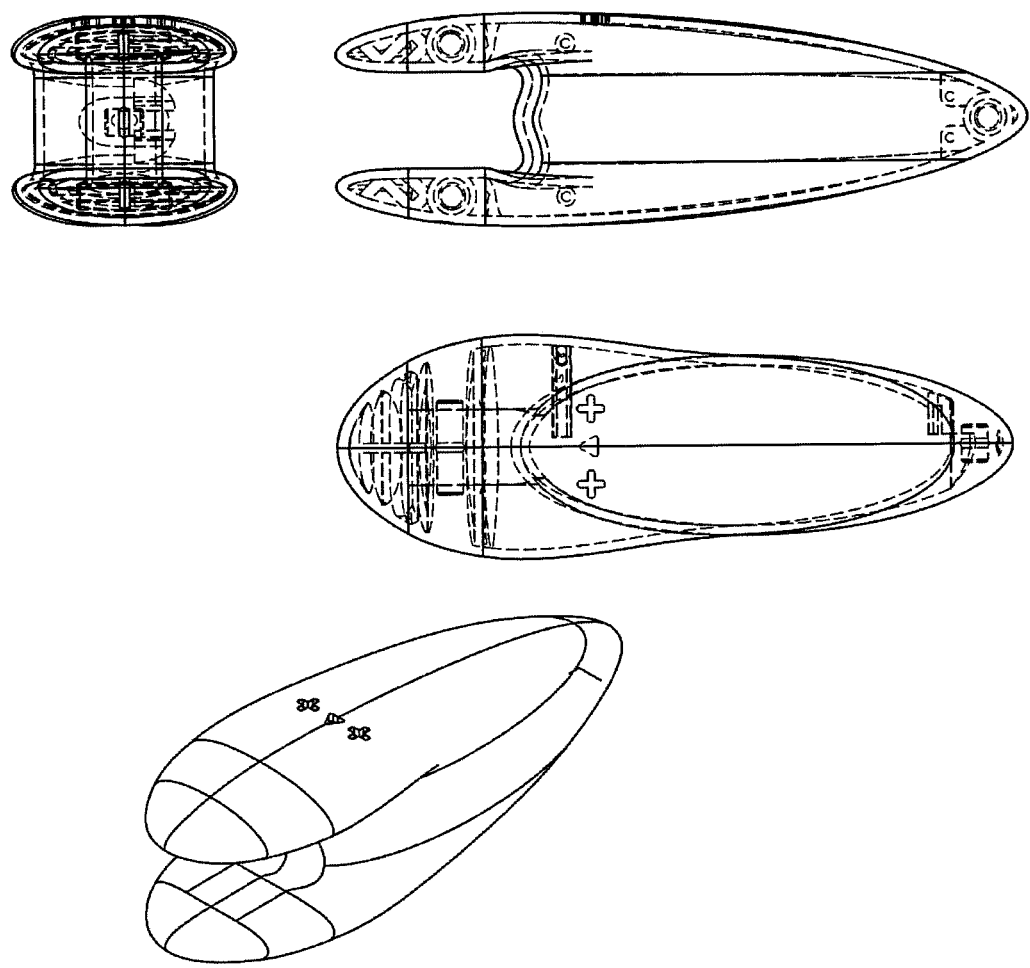
Figure 12I:
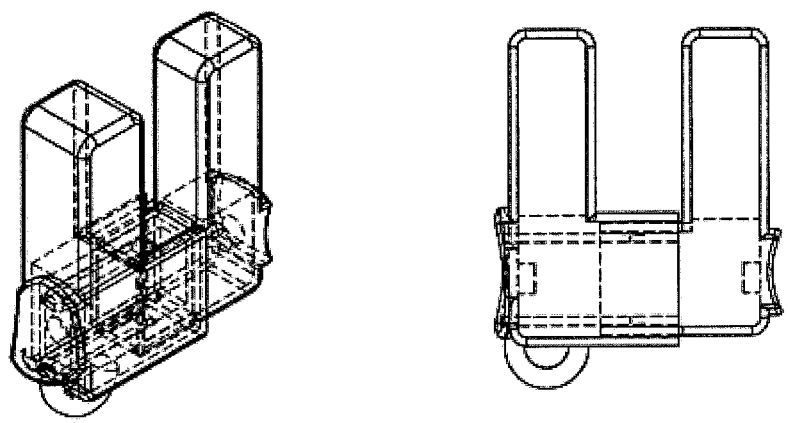
Figure 12J:
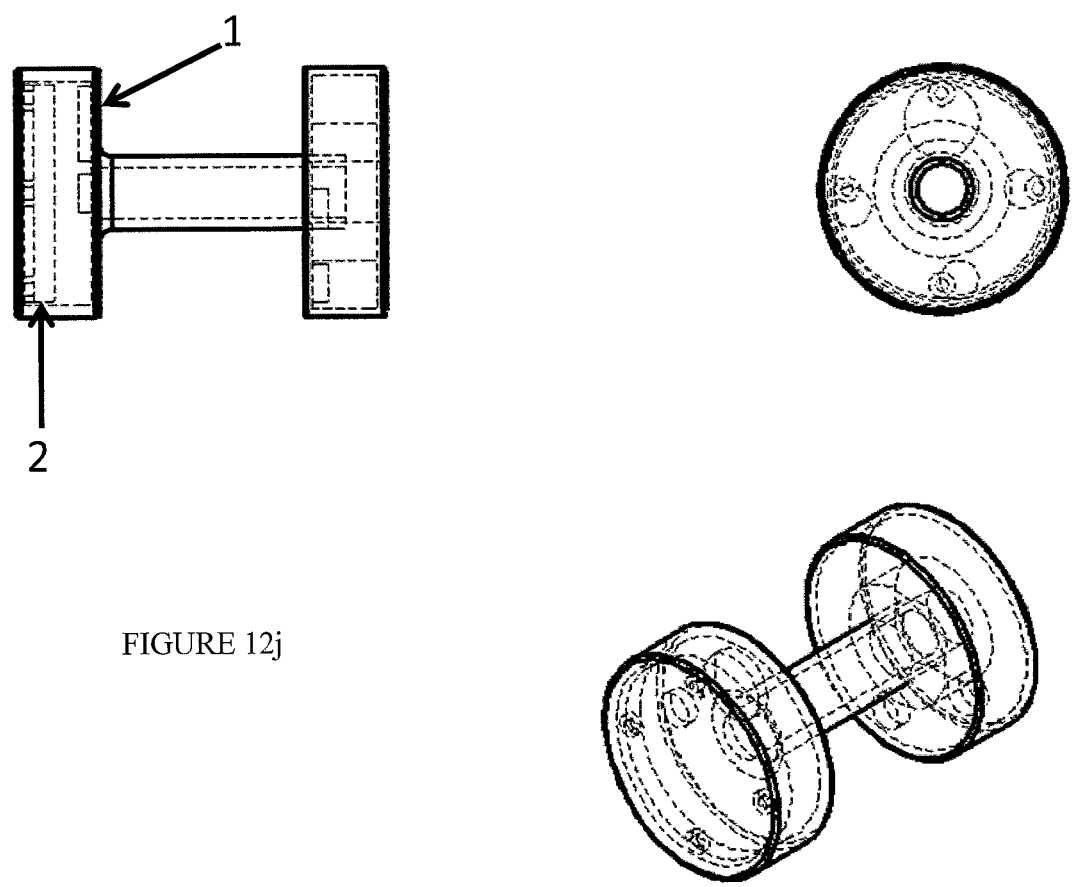
Figure 12K:
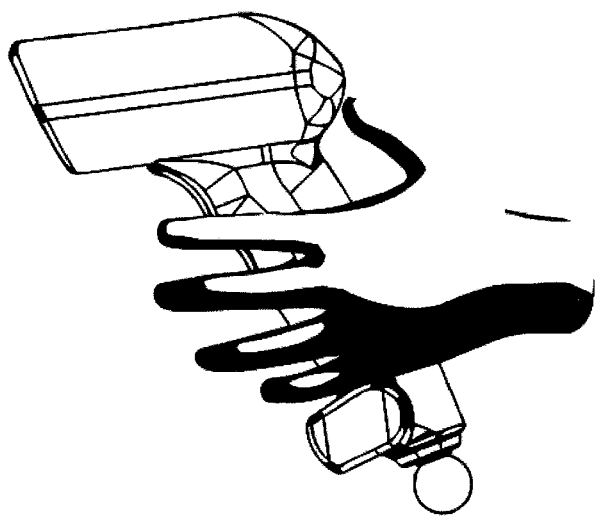
Figure 12L:
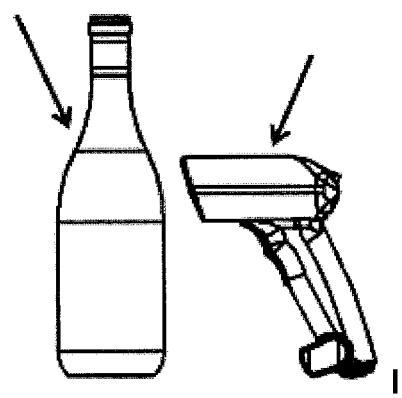
Figure 12M:
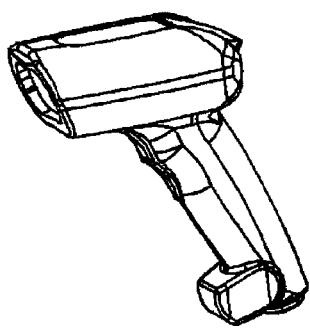

An example near-field focusing component is shown in FIG. 11f (perspective view), 11g (front view) and 11h (back view).

In embodiments, there is provided an additional layer between the antenna and the device for coupling EM radiation which shapes the electromagnetic waves emitted by the antenna. This additional layer may be considered a beam-shaping layer. The beam-shaping layer shapes the amplitude and/or phase of the radiation pattern. In embodiments, the beam-shaping layer optimises the shape of the radiation pattern for the device for coupling EM radiation in accordance with the present disclosure. In embodiments, this layer is an appropriately shaped dielectric or non-metallic material. In other embodiments, this layer is itself a metamaterial or metasurface such as a periodic combination of metal parts on a dielectric substrate. In embodiments, the beam-shaping layer comprises Teflon, liquid crystal polymer, Rogers 3000 or Rogers 400 series materials, or other dielectric materials that adds phase to the impinging waves. In embodiments, the beam shaping layer also comprises copper, alumina, or other highly conductive material.

In embodiments, there is provided a disposable biocompatible layer arranged to couple the device to a target. In embodiments, the disposable biocompatible layer may be provided for reasons of hygiene. In other embodiments, the disposable biocompatible layer may comprise a dielectric component, optionally, supporting a planar array of conducting elements. The disposable biocompatible layer may therefore be "tuned" to the rest of the device. The disposable biocompatible layer may be deformable and/or may have a morphology arranged to attach to a part of the human body. The disposable biocompatible layer may be formed from a polymer-based material.

It may therefore be understood that, in embodiments, the device is a multilayer device comprising a plurality of metallic-comprising and/or dielectric-comprising layers. Advantageously, a multilayer structure may be arranged to cover a suitably large phase range whilst maintaining high transmission. In embodiments, the structure comprises at least three metasurface layers. In embodiments, each layer has a thickness of $\lambda/200$ to $\lambda/3$, optionally, $\lambda/150$ to $\lambda/50$, further optionally, $\lambda/120$ to $\lambda/80$. Advantageously, the inventors have found that this restriction on the thickness of each layer ensures that waves of interest are not overly attenuated due to propagation (expanding beams) before reaching the target (or fully transmitting through the device). This restriction on the thickness of each layer also helps minimise the device size.

Sensor for Biological Material

In an embodiment, there is provided a wearable device that clips onto the earlobe, hand, or other body part rich in blood and non-invasively monitors changes to blood glucose levels in real time, either instantaneously or continuously. The radio wave sensors transmit and receive thousands of individual low power radio wave signals tissue that are then combined to obtain accurate blood glucose readings using algorithms. Optionally, the glucose readings are displayed within seconds on the device or they can be transmitted via Bluetooth to a mobile app, where the patient can manage the data and receive alerts. Further optionally, the data are then securely uploaded to an encrypted cloud-based historical record system, available to the patient or a doctor.

In an embodiment, there is provided non-invasive glucose measurements via the transmission and reflection of non-ionizing millimetre electromagnetic waves through the human blood. The devices in accordance with the present disclosure are applicable in the range 10 to 300 GHz. However, in an embodiment, the frequency of the waves is around the 40-100 GHz band, which is an available part of the spectrum open to medical and communication applications. Historically, this frequency band has not been adequately explored for glucose measurements.

There are two main methodologies for non-invasive glucose monitoring using electromagnetic waves. The first utilizes low-frequency radio waves, typically in the MHz or a few (up to 5) GHz region. The second utilizes much higher frequencies at the optical part of the spectrum. The fundamental limitation of both methods has always been the problem of bypassing the skin layer, causing sampling only at the interstitial fluid layer thus limiting their effective accuracy and speed. It has been reported that at the interstitial fluid layer glucose sensitivity is delayed by up to 30 minutes compared to intra-venous sampling. The interstitial fluid lies right beneath the skin and outside the blood arteries and capillaries.

Measurements in this band offer two distinct advantages that are superior to other non-invasive methods. First, the wavelength of the waves (around 5 mm in air) is large enough to allow penetration through human tissue such as the earlobe, yet simultaneously small enough to provide enough resolution of the blood regions inside it. Second, the small wavelength requires an equally small antenna to generate them.

Thus, a mobile miniaturized wireless sensor that can be continuously worn on the human body, e.g. ear, is feasible, incorporating all the necessary electronics and processing power to perform the glucose measurements.

Compared to optical methods, where the wavelength is much smaller (in the few micron range) the 40-100 GHz band is further advantageous because it generates waves with wavelength that are long enough to penetrate well into a biological sample. Water-based samples and tissue samples typically have very high loss and produce significant impedance mismatch, and thus a wave with shorter wavelength will perceive an electrically longer structure to penetrate through, attenuating significantly along the way. The inventors have identified 1000 GHz as the maximum frequency beyond which the wavelength is too short to penetrate deep enough through a biological sample without attenuating too much.

Compared to other methods of dielectric spectroscopy that utilize microwaves or radio waves, they typically operate at much lower frequencies (longer wavelengths), up to 10 GHz where the wavelength is 3 cm. These waves are long enough to perceive an electrically small sample without much attenuation. However, with some samples, they may not small enough to resolve details inside a sample, providing only averaged macroscopic information. In addition, if the sample is thin, e.g. 3 mm or less (such is the case for the earlobe), then a wave that is at least 10 times longer will be unable to sense any high-accuracy information from that sample. Thus, in an embodiment, 40 GHz is the lowest frequency below which the wavelength is too long to sense small details and ingredients in a sample with high, reproducible accuracy.

As a result, the inventors have found that 10-300 GHz, optionally 40-100 GHz, is the optimum band to produce accurate sensing measurements without attenuating the waves. More specifically, the inventors have found that two bandwidths, 59-64 and 68-72 GHz, are particularly suitable for a range of biological samples. In embodiments, the inventors have found that better results are achieved when the bandwidth is 4-6 GHz.

Many attempts have been made in the past to estimate glucose levels using resonating methods. These methods are extremely accurate, and they are commonly used for many years in characterizing materials. There is no question that they could be used to measure glucose accurately, if all other factors remained constant. However their greatest strength is also their greatest weakness: if you try it on a different person, or for any physiological skin changes (e.g. aging, during pregnancies, sweating/wet or dry skin etc.), then the measurement will provide spurious readings. The skin has pores which our body uses to maintain a constant temperature. Something as simple as moving to a hotter room will trigger the production of sweat in the glands which will throw the measurement accuracy off. The structure in accordance with the present disclosure mitigates the effects of the skin and/or allows electromagnetic radiation to substantially penetrate the skin where it would otherwise be reflected.

In embodiments, the device in accordance with the present disclosure is arranged to minimise the reflection off skin and other certain biological tissue. In embodiments, the biological material of interest is blood and the device is arranged to minimise the reflection off skin. In embodiments, there is therefore provided an antireflection coating for skin. In these embodiments, the skin may be considered a container for the biological material of interest.

FIG. 11$i$ shows a simulation result of the power penetration using a metasurface, in accordance with the present disclosure, against human skin. Specifically, FIG. 11$i$ shows the power reflected in, power transmitted and power dissipated against frequency for the structure in contact with a layer of skin 0.58 mm thick. Solid lines correspond to the setup consisting of the metasurface and the skin and dashed lines correspond to a setup consisting of the skin only without metasurface.

The total thickness of the metasurface structure is 150 µm. The addition of the metasurface produces a decrease from 39% to 0.16% in the reflected power and an increase from 56% to 94% in the dissipated power at 60 GHz. The transmitted power, increases from 4.5% to 6.3%. The main reason that a perfect transmission is not achieved is the presence of loss in the structure.

Sensor Configurations

Schematic representations of the sensor are shown in FIGS. 12$a$ to 12$m$. The sensor can be placed in body areas that are rich in blood and without many other obstructions (such as bones). In the embodiments, the locations are the earlobe, the hand (between the thumb and the index finger), between toes, on the lips, although other locations could be used. The sensor can be held in place temporarily by hand, or attached continuously.

Sensor for Food Stuff

In other embodiments, the device in accordance with the present disclosure is used to probe the properties of food stuff. That is, in embodiments, the biological material is food stuff. In other embodiments, the biological material is packaged food stuff and the device in accordance with the present disclosure is arranged and/or used to minimise reflection off the packaging. In embodiments, there is therefore provided an antireflection coating for packaging of food stuff. In embodiments, the food stuff is oil such as olive oil or composite oils containing olive oil.

System Overview

Figure 13:
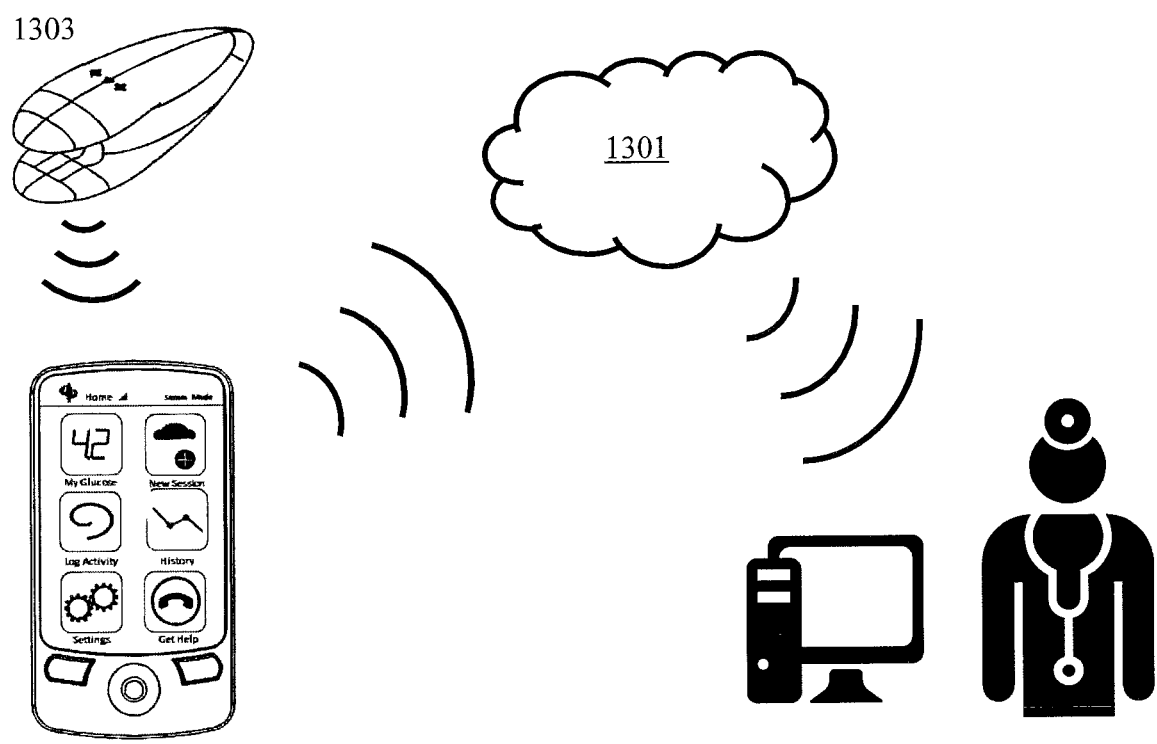
FIG. 13 is an overview of the system.

In an embodiment, there is provided a sensor system comprising a sensor 1303 that measures transmission through a sample under test (SUT), a software application (mobile, tablet, computer, etc.) that wirelessly receives the data in real time or whenever the connection becomes available, an online storage 1301 and database, and a client application/interface that displays the data to a user or third party. This is shown in FIG. 13.

The sensor comprises a transmitter and a receiver. In embodiments, the transmitter comprises of one, two, or more antennas for generating the radiation, and the metamaterial (typically placed between the antenna and the sample) to enhance the penetration through the sample.

There is therefore provided a sensor comprising: a transmitter comprising a first antenna and a first device (for coupling electromagnetic radiation, as described above) arranged to couple electromagnetic radiation emitted by the first antenna to a biological material; and a receiver comprising a second antenna and a second device (for coupling electromagnetic radiation, as described above) arrange to couple electromagnetic radiation transmitted by the biological material to the second antenna.

Figure 14A:
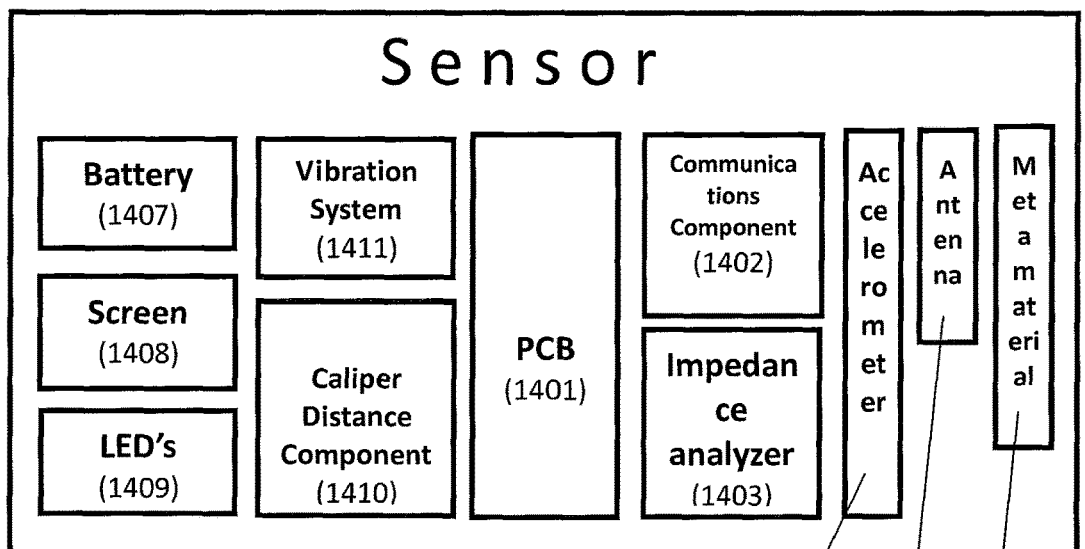
FIG. 14a shows system components of the sensor measurement device in accordance with embodiments.
Figure 14B:
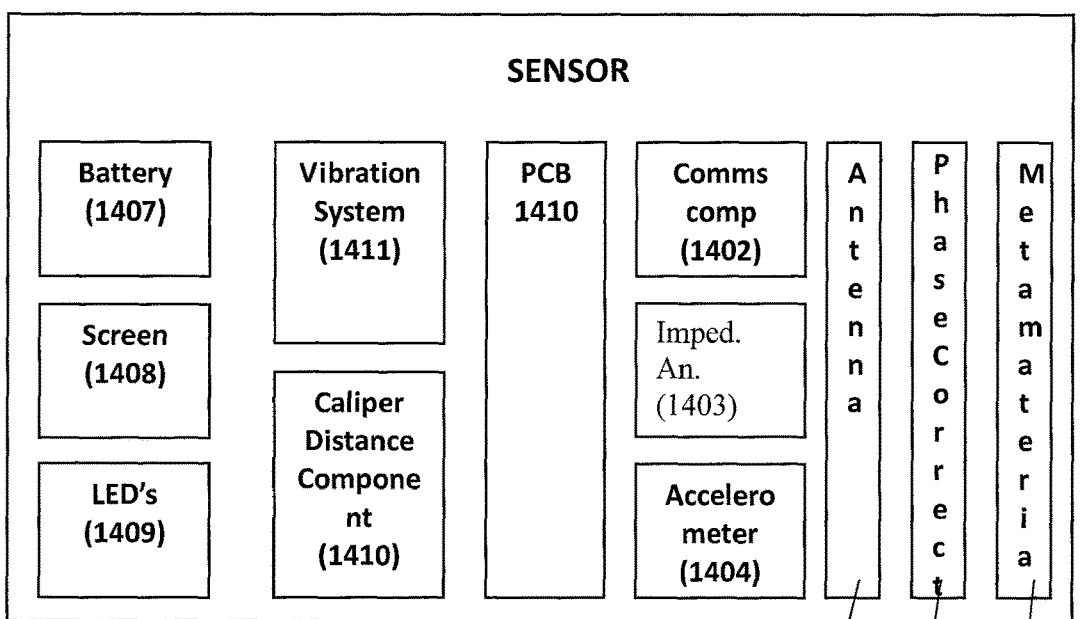
FIG. 14b shows system components of another sensor measurement device in accordance with embodiments.
Figure 15A:
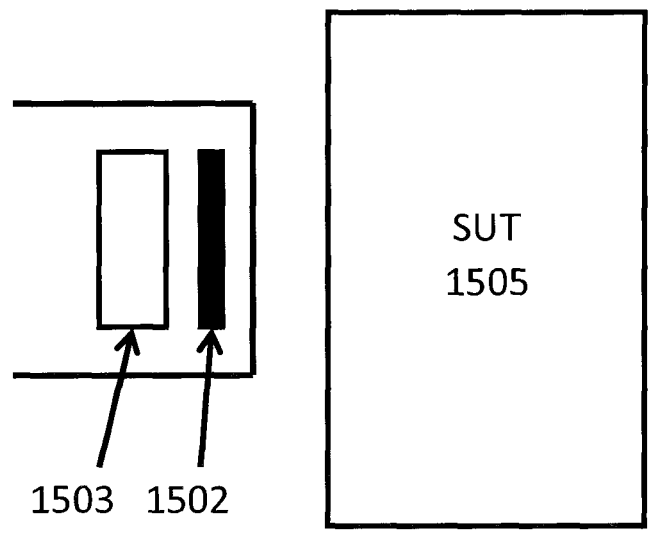
FIGS. 15a to 15d show some examples of single and dual sensors.
Figure 15B:
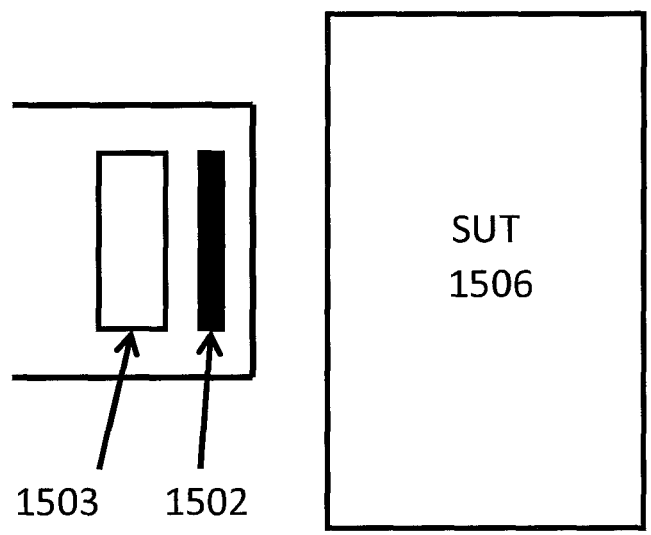
Figure 15C:
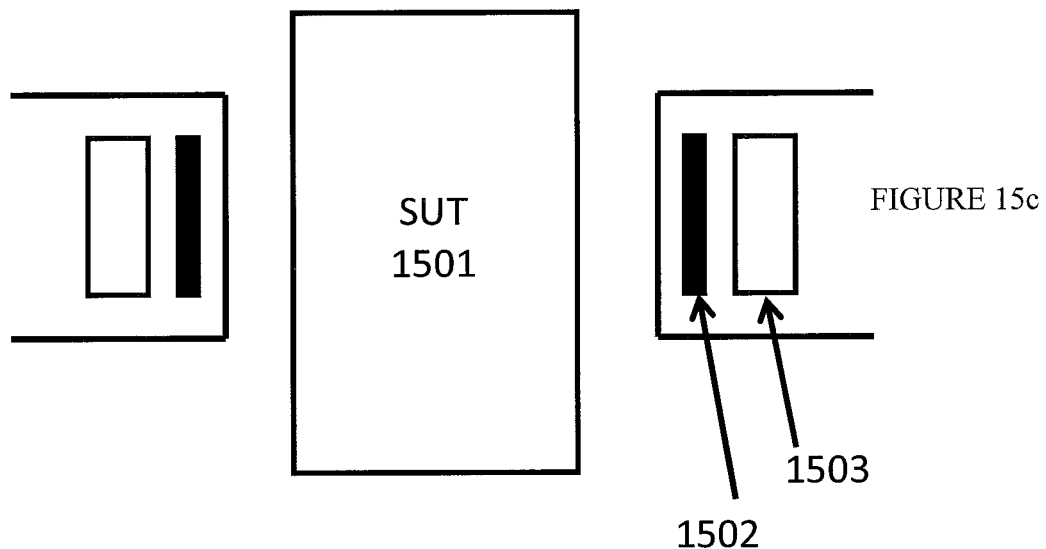
Figure 15D:
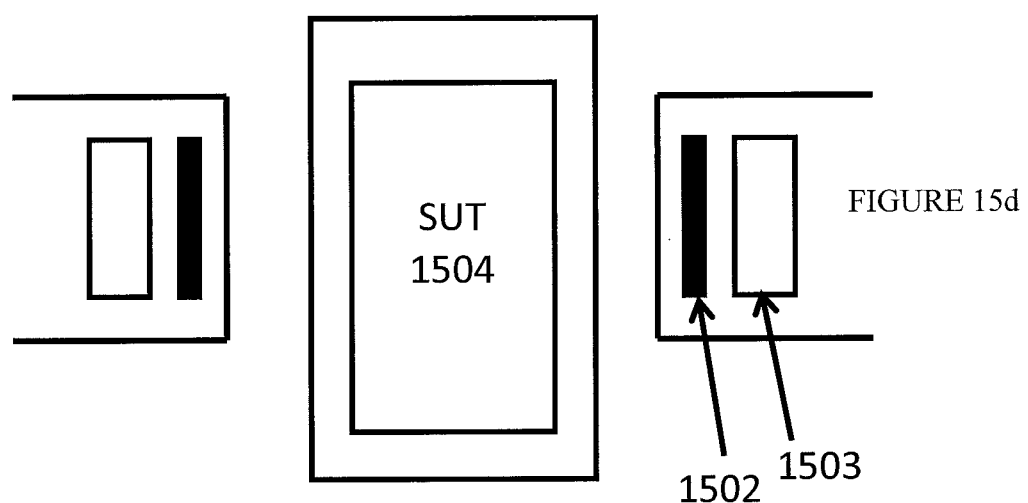

A block diagram of the components in a sensor in accordance with embodiments is shown in FIG. 14a. Some or all of the following components may be included: a battery 1407 for providing power; a screen 1408 to display the data; and LEDs 1409 to provide visual feedback; a vibration system 1411 to also provide feedback to the user; an electronic calliper component 1410 that can measure the distances between antennas; a printed circuit board 1401 that hosts the electronics; a Bluetooth or other communications component 1402 to transmit information to a receiver; an impedance analyzer 1403 to directly estimate the impedance of the sample under test; an accelerometer 1404 to sense motion; an antenna system 1405 to generate the radio wave signals; and the metamaterial component 1406 that enhances the penetration of the radiation inside the sample under test. FIG. 14b shows the components of a sensor in accordance with other embodiments including an additional beam shaping element 1450. In embodiments disclosed herein, the beam shaping element is a phase corrector by way of example only.

In an embodiment, the transmitter further comprises a detector arranged to detect electromagnetic radiation reflected by the biological material. Advantageously, this allows for more accurate measurements of the biological material to be made.

In a further embodiment, the sensor is further arranged to determine the distance between the transmitter and receiver. In another embodiment, the sensor is further arranged to determine the impedance of the biological material. Advantageously, this allows the device to work with different biological materials such as with different people. In an embodiment, the sensor further comprises an accelerometer.

The antenna, the metamaterial, or both, could be active, tunable component so as to adjust their operation depending on the electromagnetic properties (permittivity, permeability, impedance) of the sample under test. For example, when a different sample is tested that has a slightly different impedance than the sample before it, the impedance analyser will sense that and the antenna & metamaterial will be accordingly tuned to maximize the penetration through the sample. This can be achieved by integrating tunable electrical components such as variable capacitors (varactors), inductors, or resistors.

That is, in an embodiment, the sensor further comprises variable resistors and/or capacitors coupled to an antenna and/or metamaterial to provide tunability.

The sample under test may or may not be placed inside an enclosure or container. The skin can be considered as a container for animal or human tissue. In an embodiment, the biological material is human or animal tissue. In an embodiment, the sensor is wearable. In a further embodiment, the sensor is arranged to be worn on a hand, a foot, an ear or a lip or wherein the sensor is handheld.

In an embodiment, the biological material is food stuff. In an embodiment, the food stuff comprises at least one selected from the group comprising oil, milk, wine, coffee and fruit juice and/or the food stuff is bound by a container, optionally, a bottle or carton. In an embodiment, the container comprises glass and/or plastic.

There is also provided a system comprising the sensor and further comprising: a wireless receiver arranged to receive data related to the biological material from the sensor; a software application operating on a device remote to the sensor, the software application arranged to process the data; and an interface arranged to display the data and/or information related to the data. Advantageously, it may therefore be possible to remotely monitor a sample. For example, a medical professional may be able to remotely measure the blood sugar level of a patient.

Figure 16:
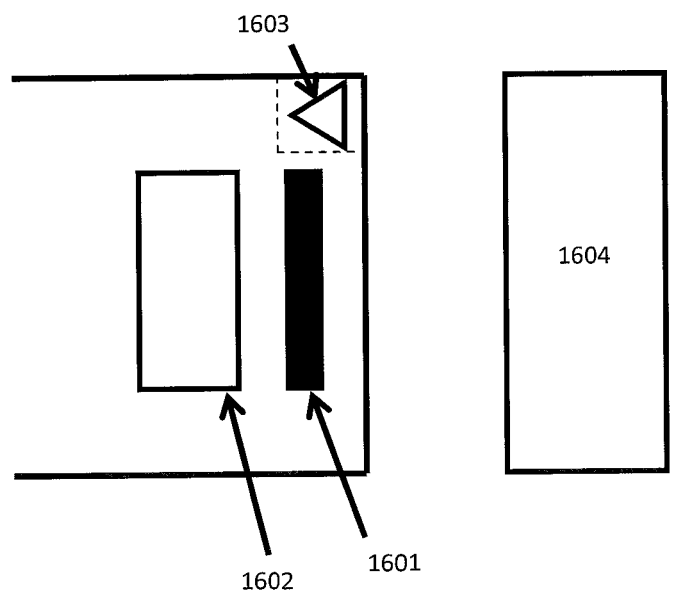
FIG. 16 shows a tuning antenna with an impedance analyser.
Figure 17A:
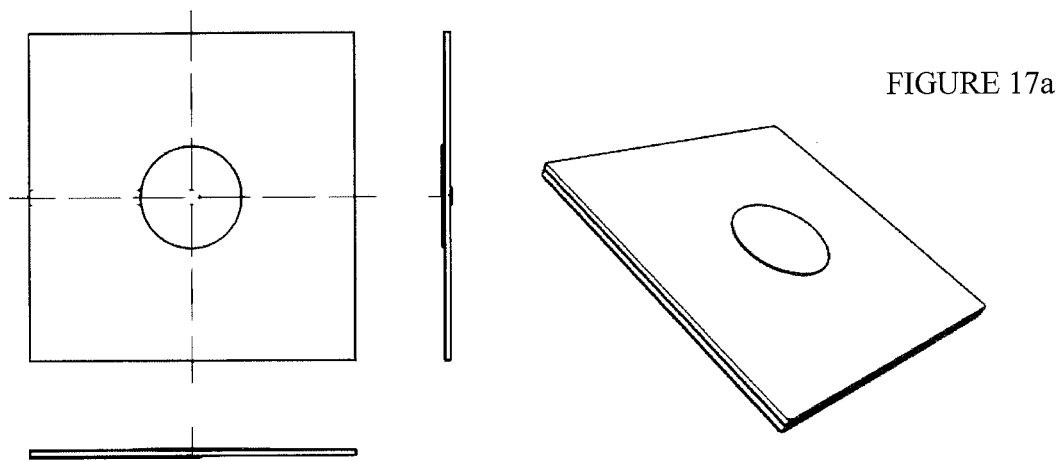
FIGS. 17a to 17c show the sensor in use.
Figure 17B:
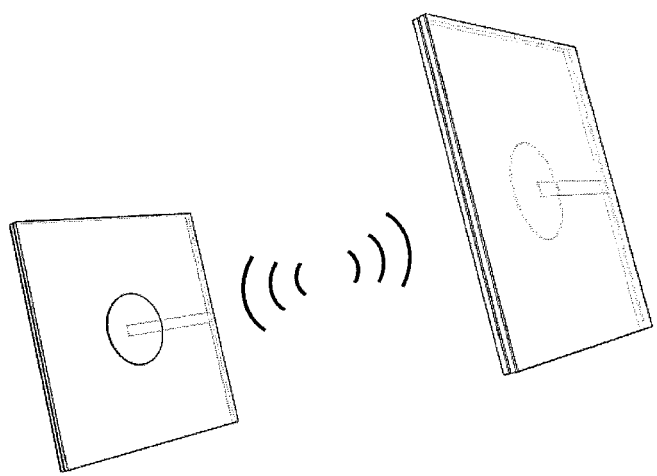
Figure 17C:
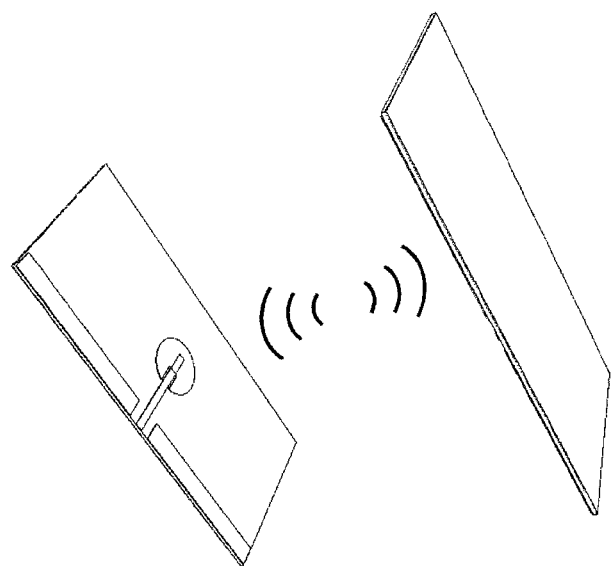
Figure 18A:
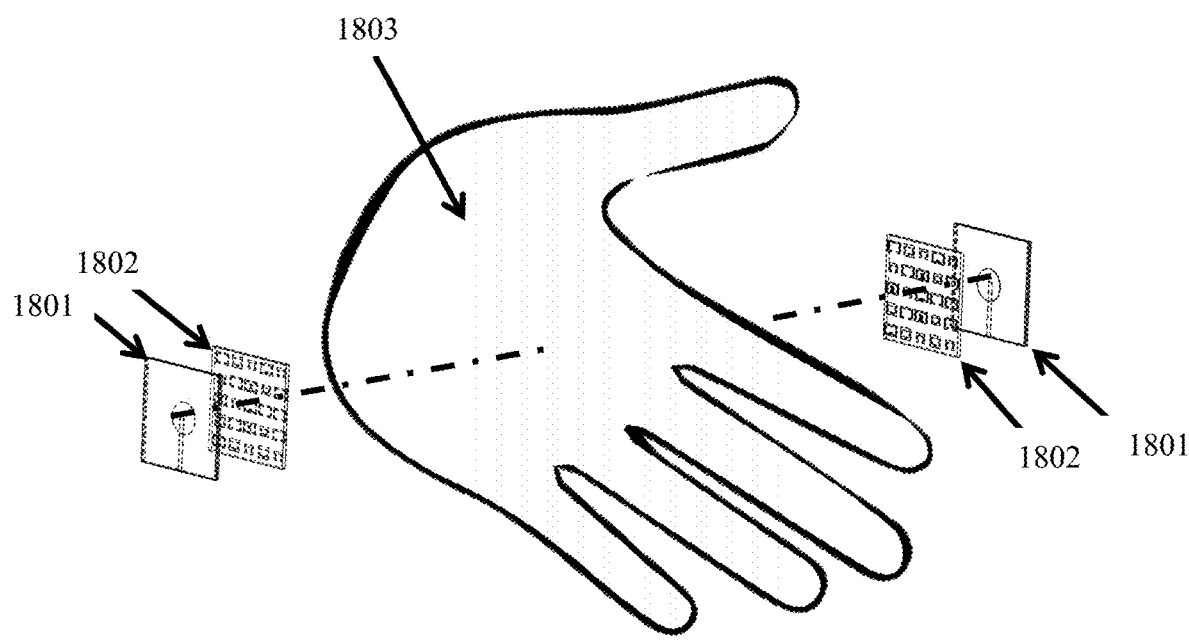
FIGS. 18a and 18b are isometric views of a measurement system through a human hand.
Figure 18B:
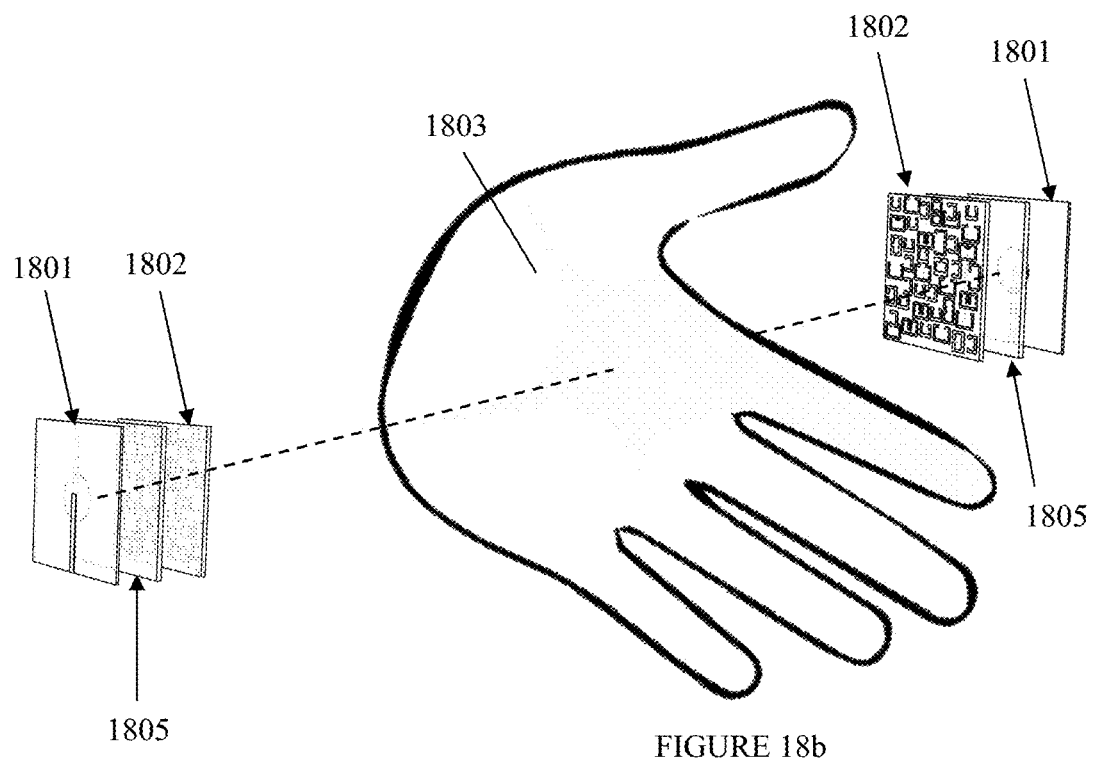

FIGS. 15a to 15d show some examples of samples under test 1501, 1504, 1505, 1506 with single and dual antenna 1503 and metamaterial 1502 arrangements. FIG. 16 shows a tuning antenna 1602 including an impedance analyser 1603, metasurface 1601 for probing a sample under test 1604.

FIGS. 17a to 17c and 18 illustrate an example device in operation. FIG. 18a shows a sensor comprising two antennas 1801 and two metasurfaces 1802 arranged to improve coupling of electromagnetic radiation into and out of a human hand 1803. FIG. 18b shows the sensor with additional phase corrector components 1805.

Figure 19A:
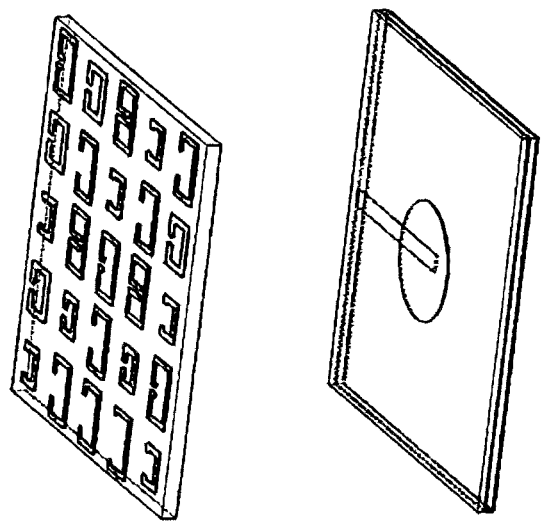
FIGS. 19a and 19b are exploded views of a metasurface with antenna configuration in (a) period and (b) non-periodic patterns.
Figure 19B:
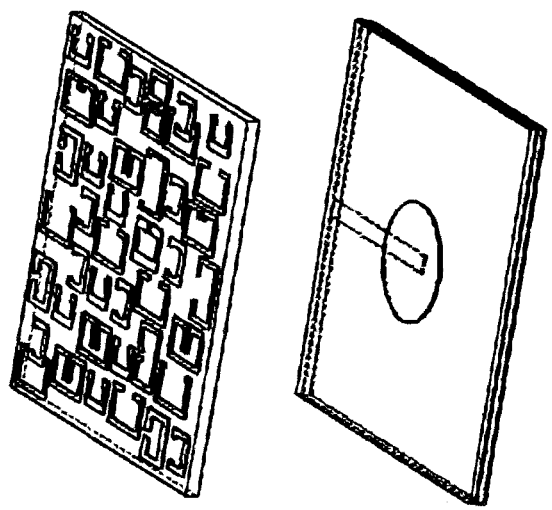

FIG. 19 shows exploded views of metasurface with antenna configuration in periodic pattern (Top) and non-periodic pattern (Bottom).

Figure 20:
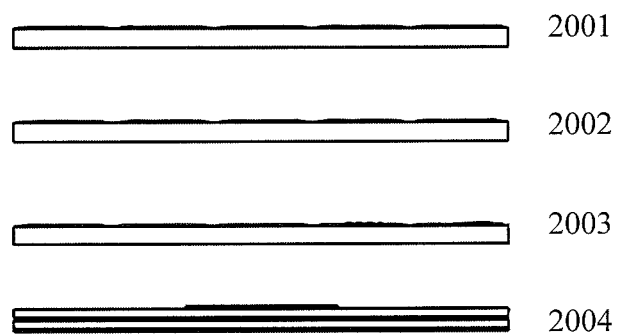
FIG. 20 is an exploded side view of antenna and three metasurface layers.

FIG. 20 shows a layered device in accordance with embodiments comprising three metasurface layers 2001-2003 and an antenna layer 2004.

Advantageously, the device in accordance with embodiments of the present disclosure is passive. That is, it does not require a power supply. The device may therefore increase the overall energy efficiency.

There is provided an antireflective medium for a glucose sensor, the antireflective medium comprising a metasurface. There is also provided an antireflective coating for a food stuff container, the antireflective coating comprising a metasurface.

Although aspects and embodiments have been described above, variations can be made without departing from the inventive concepts disclosed herein.

EXAMPLE EXPERIMENTAL RESULTS

The two examples presented are glucose sensing in calibrated water-based samples, and oil sensing in oil mixtures. The measurements were performed in the 50-75 GHz band. The quantities presented are retrieved from the raw transmission and reflection recorded signals after applying noise filtering and other signal processing algorithmic operations.

Example 1: Glucose Sensing

Figure 21:
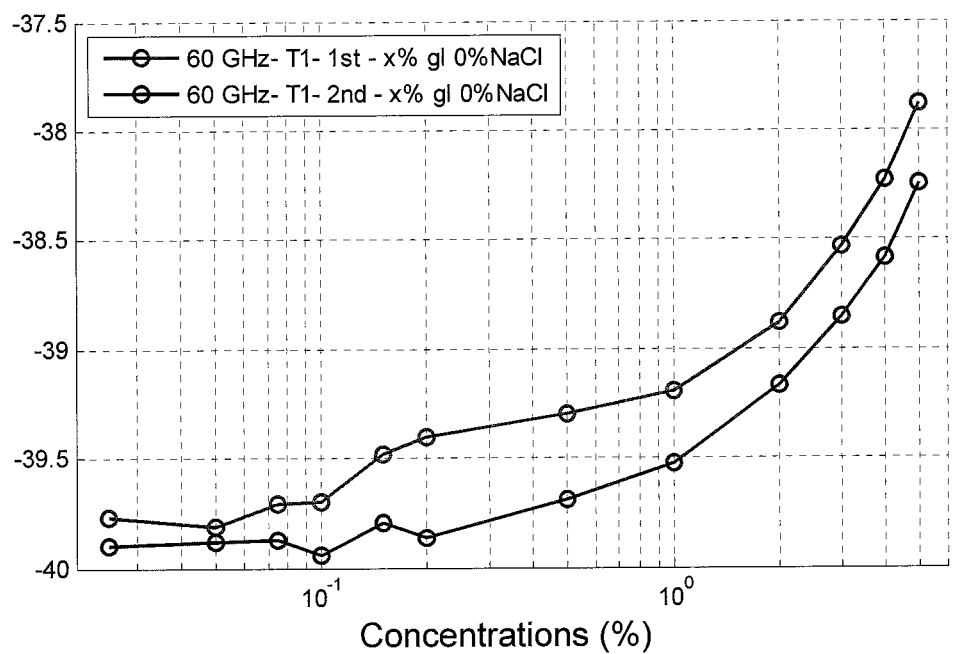
FIG. 21 plots an output signal as a function of glucose concentration in a sample containing water and glucose.

FIG. 21 shows the correlation between the glucose concentration and the processed signal, repeated in two independently prepared sample solutions around 60 GHz. The results indicate the repeatability of the method and the algorithm utilized.

Figure 22:
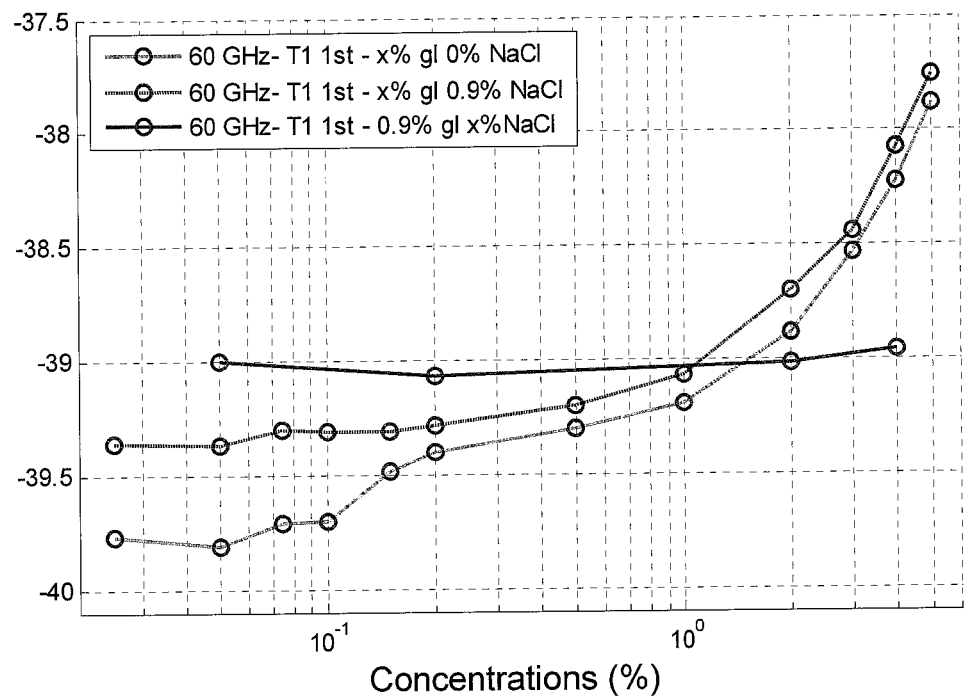
FIG. 22 plots an Output signal as a function of concentration in samples containing water and glucose, water & glucose & salt, and water & salt.

FIG. 22 compares the measurements obtained for three different types of sample: samples consisting of water and varying amounts of glucose, sample consisting of water, salt (NaCl) and varying amounts of glucose and samples consisting of water, varying amounts of salt and glucose. The results demonstrate that the three different solutions and their corresponding concentrations can be completely distinguished from each other. The purpose of using salt is that is a more realistic representation of human blood.

Figure 23:
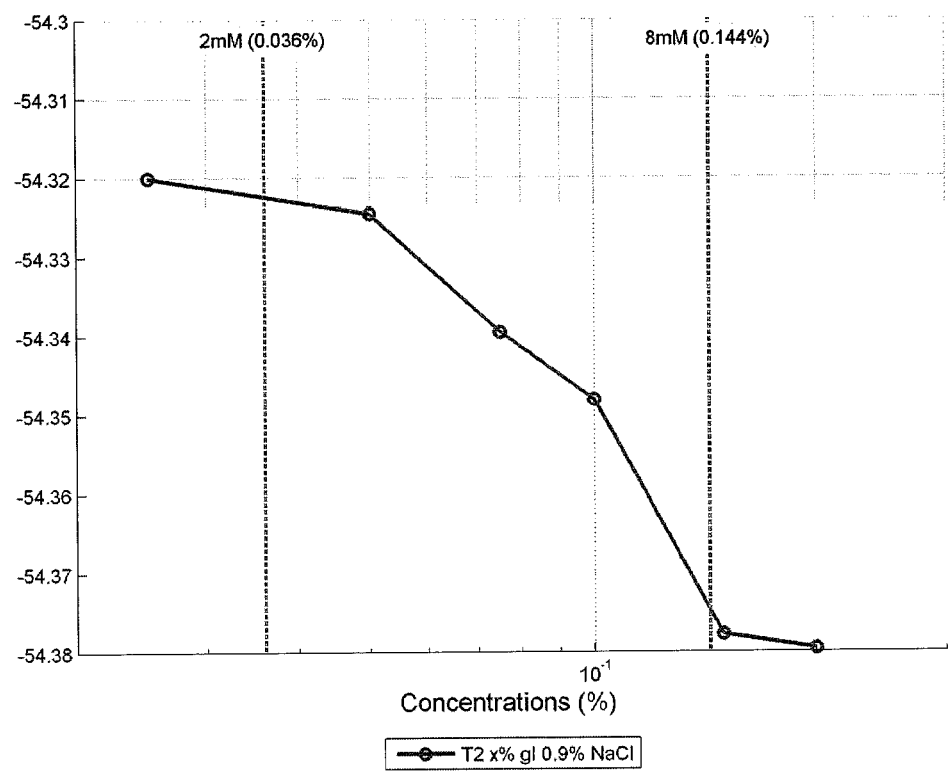
FIG. 23 plots an output signal as a function of glucose concentration in samples containing water and glucose in very small amounts.

FIG. 23 presents the processed signal as a function of glucose concentration for very low concentrations (the normal range for adults is between 4 and 8 mMol/L) at a frequency of 68 GHz. It demonstrates that very low glucose concentrations can be quantified.

Example 2: Oil Sensing

In this example the unknown concentration of palm kernel oil in a mixture of palm kernel oil and rapeseed oil was determined for two different experimental runs. The processed data are fitted with a linear equation, which can be used to exactly determine the concentration of each oil species in the mixture.

Figure 24:
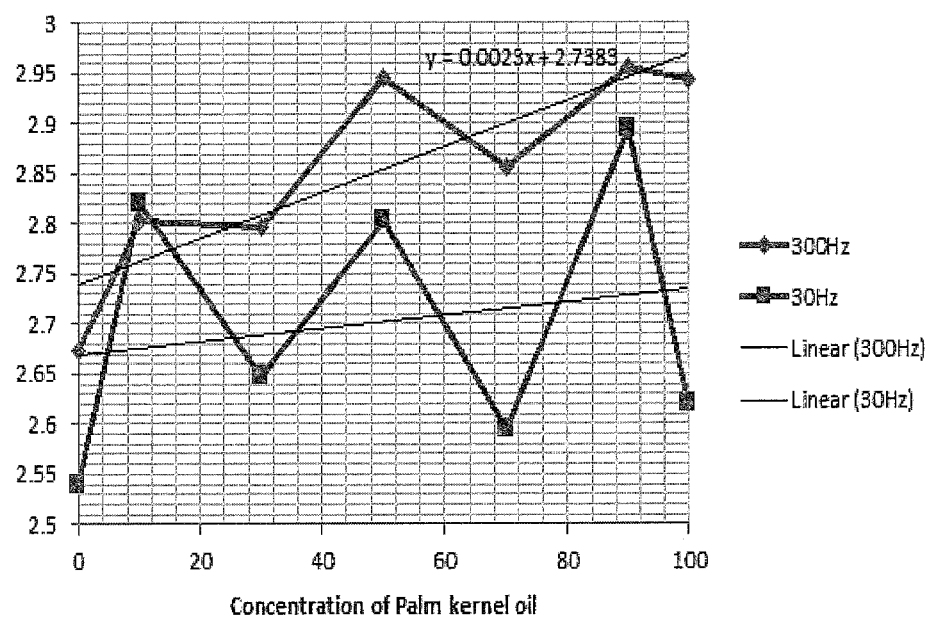
FIG. 24 shows an output signal as a function of the concentration of palm kernel oil in a mixture of palm kernel and rapeseed oil.

FIG. 24 shows output signal as a function of the concentration of palm kernel oil in a mixture of palm kernel and rapeseed oil.

Figure 25:
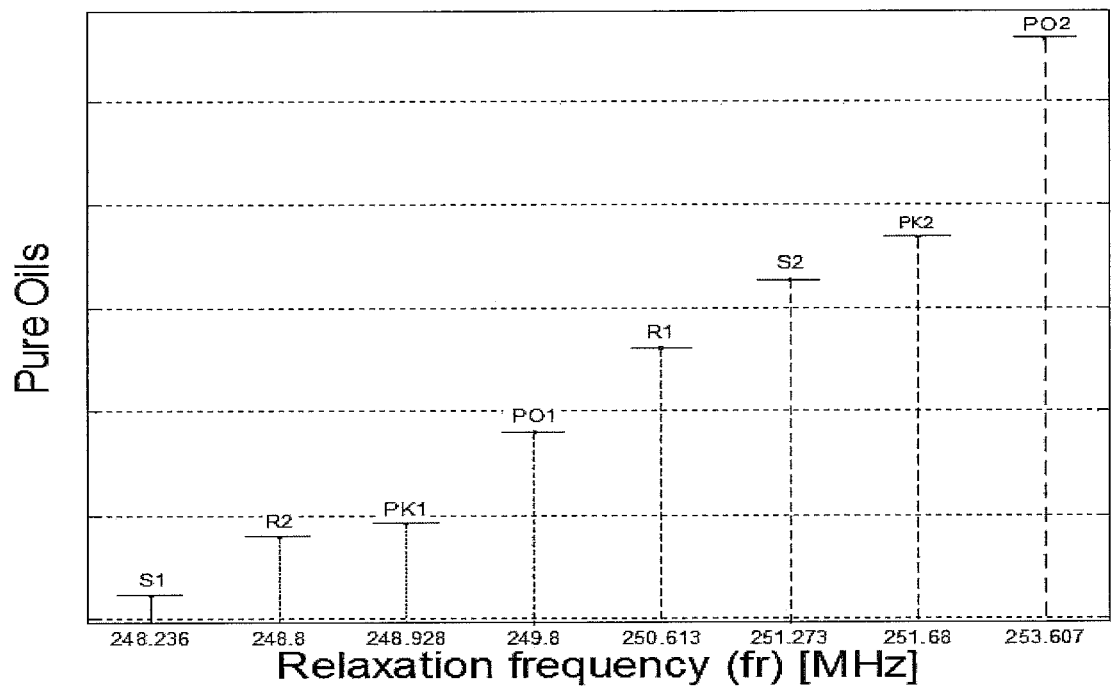
FIG. 25 shows relaxation frequencies of the Cole-Cole model for different oil species.

FIG. 25 shows the processed signals from the radio wave reflection measurements are fitted with an analytic Cole-Cole model, estimating the relaxation frequency of the model. Each oil species exhibits a characteristic relaxation frequency, which can be used to identify an unknown oil species in a sample. In this case a single sensor is used against the sample.

The sensor in accordance with embodiments is therefore highly effective at determining the concentration of oils in a mixture of oils.

The invention claimed is:
1. A sensor measurement device, comprising:
  a transmitter comprising:
    a first antenna configured to generate electromagnetic radiation to penetrate a biological material, the electromagnetic radiation having a first wavelength between 30 micrometers and 3 centimeters; and
    a first anti-reflection device arranged to transmit electromagnetic radiation of the first wavelength emitted by the first antenna into the biological material, the first anti-reflection device comprising a first metamaterial comprising:
      a substrate component having a thickness no greater than the first wavelength of the electromagnetic radiation; and
      a plurality of elements supported by the substrate component, wherein the plurality of elements are spaced apart from one another across the substrate component, wherein each element has a first dimension no greater than the first wavelength of the electromagnetic radiation and wherein at least two of the elements of the plurality of elements differ in shape and/or size; and
  a receiver comprising a second antenna configured to receive electromagnetic radiation from the biological material,
  wherein the transmitter and receiver are arranged for the biological material to be positioned in a radiation path between the first antenna and the second antenna and with the first anti-reflection device in a radiation path between the first antenna and the biological material, such that electromagnetic radiation of the first wavelength can be transmitted from the first anti-reflection device into the biological material and electromagnetic radiation from the biological material can be received by the second antenna; and
  wherein the sensor measurement device is a self-contained unit physically associating together the transmitter and the receiver.

2. A sensor measurement device as claimed in claim 1 wherein in the first anti-reflection device the first dimension is the direction for propagation of the electromagnetic radiation.

3. A sensor measurement device as claimed in claim 1 wherein in the first anti-reflection device at least one of the elements of the plurality of elements has an irregular shape or wherein the elements of the plurality of elements have an irregular shape.

4. A sensor measurement device as claimed in claim 1 wherein the biological material is bound by a container, and wherein the first anti-reflection device is configured to transmit electromagnetic radiation of the first wavelength into the biological material from a position outside the container.

5. A sensor measurement device as claimed in claim 1 wherein in the first anti-reflection device at least a subset of the elements are arranged in an irregular array.

6. A sensor measurement device as claimed in claim 1 wherein in the first anti-reflection device the elements are arranged in an irregular array.

7. A sensor measurement device as claimed in claim 1 wherein in the first anti-reflection device the substrate component is a dielectric and the elements are conductive.

8. A sensor measurement device as claimed in claim 7 wherein in the first anti-reflection device the elements are metallic.

9. A sensor measurement device as claimed in claim 1 wherein in the first anti-reflection device the substrate component is conductive and the elements are a dielectric.

10. A sensor measurement device of claim 9 wherein the substrate component is metallic.

11. A sensor measurement device as claimed in claim 1 wherein in the first anti-reflection device the plurality of elements are collectively arranged to resonate at a first wavelength of the electromagnetic radiation.

12. A sensor measurement device as claimed in claim 1 wherein the first anti-reflection device further comprises a second metamaterial coupled to the first metamaterial, wherein the second metamaterial comprises:
  a substrate component having a thickness no greater than a second wavelength of the electromagnetic radiation, wherein the second wavelength is between 30 micrometers and 3 centimeters; and
  a plurality of elements supported by the substrate component, wherein each element has a first dimension no greater than a second wavelength of the electromagnetic radiation and at least two of the elements of the plurality of elements are non-identical.

13. A sensor measurement device as claimed in claim 12 wherein in the first anti-reflection device the second metamaterial is arranged, in cooperation with the first metamaterial, to resonate at a second wavelength of the electromagnetic radiation.

14. A sensor measurement device as claimed in claim 13 wherein the first wavelength is different to the second wavelength.

15. A sensor measurement device as claimed in claim 1 wherein the first anti-reflection device comprises a plurality of metallic-comprising and/or dielectric-comprising layers.

16. A sensor measurement device as claimed in claim 1 wherein the electromagnetic radiation of the first wavelength has a frequency of 40 to 100 GHz.

17. A sensor measurement device as claimed in claim 1 wherein the transmitter further comprises a detector arranged to detect electromagnetic radiation reflected by the biological material.

18. A sensor measurement device as claimed in claim 1 further comprising an electronic calliper arranged to determine the distance between the transmitter and receiver.

19. A sensor measurement device as claimed in claim 1 further comprising an impedance analyser arranged to determine the impedance of the biological material.

20. A sensor measurement device as claimed in claim 1 further comprising an accelerometer.

21. A sensor measurement device as claimed in claim 1 further comprising variable resistors and/or capacitors coupled to one or more of the first antenna, the second antenna, the metamaterial of the first device and the metamaterial of the second device, to provide tunability.

22. A sensor measurement device as claimed in claim 1 wherein the biological material is human or animal tissue bound by skin, and wherein the first anti-reflection device is configured to transmit electromagnetic radiation of the first wavelength from the first antenna, through the skin and into the human or animal tissue.

23. A sensor measurement device as claimed in claim 1 wherein the human or animal tissue is blood and the sensor is arranged to measure glucose and/or blood sugar level.

24. A sensor measurement device as claimed in claim 1 wherein the sensor is wearable.

25. A sensor measurement device as claimed in claim 1 wherein the sensor is arranged to be worn on a hand, a foot, an ear or a lip or wherein the sensor is handheld.

26. A system comprising the sensor measurement device as claimed in claim 1 further comprising:
   a wireless receiver arranged to receive data related to the biological material from the sensor measurement device;
   a software application operating on a device remote to the sensor, the software application arranged to process the data; and
   an interface arranged to display the data and/or information related to the data.

27. A sensor measurement device according to claim 1, wherein the receiver further comprises a second anti-reflection device arranged to transmit electromagnetic radiation of the first wavelength from the biological material to the second antenna, the second anti-reflection device comprising a metamaterial comprising:
   a substrate component having a thickness no greater than the first wavelength; and
   a plurality of elements supported by the substrate component, wherein the plurality of elements are spaced apart from one another across the substrate component, wherein each element has a first dimension no greater than the first wavelength and wherein at least two of the elements of the plurality of elements differ in shape and/or size.

28. A method of coupling electromagnetic radiation into a biological material using a sensor measurement device according to claim 27, the method comprising:
   providing electromagnetic radiation having the first wavelength from the first antenna;
   coupling, by the first anti-reflection device, electromagnetic radiation having the first wavelength from the first antenna into the biological material; and
   coupling, by the second anti-reflection device, electromagnetic radiation having the first wavelength from the biological material to the second antenna.

29. A sensor according to claim 1, wherein the first wavelength corresponds to a frequency of 40-100 GHz.

30. A method of coupling electromagnetic radiation into a biological material of a human or animal using a sensor measurement device, the sensor measurement device comprising:
   a transmitter comprising:
      a first antenna configured to generate electromagnetic radiation to penetrate a biological material, the electromagnetic radiation having a first wavelength between 30 micrometers and 3 centimeters; and
      a first anti-reflection device arranged to transmit electromagnetic radiation of the first wavelength emitted by the first antenna into the biological material, the first anti-reflection device comprising a first metamaterial comprising:
         a substrate component having a thickness no greater than the first wavelength of the electromagnetic radiation; and
         a plurality of elements supported by the substrate component, wherein the plurality of elements are spaced apart from one another across the substrate component, wherein each element has a first dimension no greater than the first wavelength of the electromagnetic radiation and wherein at least two of the elements of the plurality of elements differ in shape and/or size; and
   a receiver comprising a second antenna configured to receive electromagnetic radiation from the biological material,
   the sensor measurement device being a single a self-contained unit physically associating together the transmitter and the receiver,
the method comprising:
   positioning the sensor measurement device with respect to the human or animal such that the transmitter is disposed outside the human or animal, and such that the receiver is disposed outside the human or animal;
   providing electromagnetic radiation having the first wavelength from the first antenna to the first anti-reflection device;
   transmitting, by the first anti-reflection device, electromagnetic radiation having the first wavelength from the first antenna into the biological material;
   receiving, by the receiver, electromagnetic radiation from the biological material; and
   characterizing the biological material based on the received radiation.

31. A method according to claim 30, further comprising receiving electromagnetic radiation of the first wavelength from the biological material at the second antenna.

32. A non-invasive sensor measurement device for sensing a property of a biological tissue of a human or animal, the sensor measurement device comprising:
   a transmitter comprising:
      a first antenna configured to generate electromagnetic radiation to penetrate the biological material, the electromagnetic radiation having a first wavelength between 30 micrometers and 3 centimeters; and
      a first anti-reflection device arranged to transmit electromagnetic radiation of the first wavelength emitted by the first antenna into the biological material, the first anti-reflection device comprising a first metamaterial comprising:
         a substrate component having a thickness no greater than the first wavelength of the electromagnetic radiation; and
         a plurality of elements supported by the substrate component, wherein the plurality of elements are spaced apart from one another across the substrate component, wherein each element has a first dimension no greater than the first wavelength of the electromagnetic radiation and wherein at least two of the elements of the plurality of elements differ in shape and/or size; and a receiver comprising a second antenna configured to receive electromagnetic radiation from the biological material, wherein the transmitter and receiver are configured to be positioned outside a skin of the human or animal such that the biological material is disposed in a radiation path between the first antenna and the second antenna and with the first anti-reflection device in a radiation path between the first antenna and the biological material, such that radiation of the first wavelength can be transmitted from the first anti-reflection device into the biological material and electromagnetic radiation from the biological material can be received by the second antenna; and wherein the sensor measurement device is a self-contained wearable device or is a self-contained handheld device.

* * * * *

UNITED STATES PATENT AND TRADEMARK OFFICE
CERTIFICATE OF CORRECTION

PATENT NO. : 11,298,052 B2
APPLICATION NO. : 15/121364
DATED : April 12, 2022
INVENTOR(S) : Georgios Palikaras, Efthymios Kallos and Helena Cano Garcia It is certified that error appears in the above-identified patent and that said Letters Patent is hereby corrected as shown below:

In the Claims

Claim 30, Line 29, delete "a single" after "the sensor measurement device being".

Signed and Sealed this
Twentieth Day of December, 2022

Katherine Kelly Vidal
*Director of the United States Patent and Trademark Office*